(12) United States Patent
Frigg et al.

(10) Patent No.: US 8,808,296 B2
(45) Date of Patent: Aug. 19, 2014

(54) METHODS OF SPINAL FIXATION AND INSTRUMENTATION

(75) Inventors: Robert Frigg, Bettlach (CH); Martin Schnider, Subingen (CH); Stefan Schwer, Loerrach (DE)

(73) Assignee: DePuy Synthes Products, LLC, Raynham, MA (US)

( * ) Notice: Subject to any disclaimer, the term of this patent is extended or adjusted under 35 U.S.C. 154(b) by 611 days.

(21) Appl. No.: 13/039,786

(22) Filed: Mar. 3, 2011

(65) Prior Publication Data

US 2011/0152940 A1 Jun. 23, 2011

Related U.S. Application Data

(63) Continuation of application No. 11/213,041, filed on Aug. 25, 2005, now Pat. No. 7,909,830.

(51) Int. Cl.
*A61B 17/90* (2006.01)

(52) U.S. Cl.
USPC ............. 606/86 A; 606/96; 606/104; 606/914

(58) Field of Classification Search
USPC ............. 606/86 A, 96, 97, 98, 104, 914, 916
See application file for complete search history.

(56) References Cited

U.S. PATENT DOCUMENTS

| | | | |
|---|---|---|---|
| 1,889,330 A | 11/1932 | Humes et al. | |
| 1,903,581 A | 4/1933 | Turner | |
| 1,925,385 A | 9/1933 | Humes et al. | |
| 2,317,887 A | 4/1943 | Crollie | |
| 2,444,758 A | 7/1948 | Stillbach | |
| 2,483,396 A | 10/1949 | Benson | |
| 2,682,422 A | 6/1954 | McBride | |
| 4,007,976 A | 2/1977 | Knecht | |
| 4,333,456 A | 6/1982 | Webb | |
| 4,335,715 A | 6/1982 | Kirkley | |

(Continued)

FOREIGN PATENT DOCUMENTS

| | | |
|---|---|---|
| AU | 13672/95 | 3/1995 |
| DE | 4238339 | 5/1994 |

(Continued)

OTHER PUBLICATIONS

International Search Report for PCT/US2006/033225 dated Apr. 17, 2007.

(Continued)

*Primary Examiner* — Jerry Cumberledge
(74) *Attorney, Agent, or Firm* — Baker & Hostetler LLP

(57) ABSTRACT

A method for performing spinal fixation and instrumentation. A first incision may be made through the skin and a passageway may be created to the spine. A screw may be inserted through the passageway and into a vertebrae. The screw may have a head portion including a channel. An insertion guide may be operable connected to the screw. The insertion guide may have first and second longitudinal slots. Additional screws may each be inserted through separate incisions or through the first incision. Insertion guides may be operably connected to a head portion of each screw. A sleeve may be positioned into one insertion guide in a first position to guide a rod through at least one other insertion guide. The sleeve may be rotated to a second position to allow the rod to move down the slots of the insertion guide(s) and into the head portion of the screw.

16 Claims, 24 Drawing Sheets

(56) References Cited

U.S. PATENT DOCUMENTS

| | | |
|---|---|---|
| 4,409,968 A | 10/1983 | Drummond |
| 4,545,374 A | 10/1985 | Jacobson |
| 5,015,247 A | 5/1991 | Michelson |
| 5,171,279 A | 12/1992 | Mathews |
| 5,242,443 A | 9/1993 | Kambin |
| 5,352,231 A | 10/1994 | Brumfield et al. |
| 5,439,464 A | 8/1995 | Shapiro |
| 5,667,513 A | 9/1997 | Torrie et al. |
| 5,720,751 A | 2/1998 | Jackson |
| 5,782,830 A | 7/1998 | Farris |
| 5,810,878 A | 9/1998 | Burel et al. |
| 5,910,141 A | 6/1999 | Morrison et al. |
| 5,941,885 A * | 8/1999 | Jackson ............ 606/104 |
| 5,951,559 A | 9/1999 | Burkhart |
| 5,964,761 A | 10/1999 | Kambin |
| 6,139,549 A | 10/2000 | Keller |
| 6,183,472 B1 | 2/2001 | Lutz |
| 6,200,322 B1 | 3/2001 | Branch et al. |
| 6,224,603 B1 | 5/2001 | Marino |
| 6,235,028 B1 | 5/2001 | Brumfield et al. |
| 6,251,112 B1 | 6/2001 | Jackson |
| 6,360,750 B1 | 3/2002 | Gerber et al. |
| 6,415,693 B1 | 7/2002 | Simon et al. |
| 6,440,133 B1 | 8/2002 | Beale |
| 6,520,907 B1 | 2/2003 | Foley et al. |
| 6,530,926 B1 | 3/2003 | Davison |
| 6,530,929 B1 | 3/2003 | Justis et al. |
| 6,579,291 B1 | 6/2003 | Keith et al. |
| 6,610,065 B1 | 8/2003 | Branch et al. |
| 6,626,905 B1 | 9/2003 | Schmiel et al. |
| 6,648,888 B1 | 11/2003 | Shluzas |
| 6,695,852 B2 | 2/2004 | Gleason |
| 6,743,231 B1 | 6/2004 | Gray et al. |
| 6,800,084 B2 | 10/2004 | Davison et al. |
| 6,821,277 B2 | 11/2004 | Teitelbaum |
| 6,849,064 B2 | 2/2005 | Hamada |
| 6,863,464 B1 | 3/2005 | Niklaus |
| 6,929,606 B2 | 8/2005 | Ritland |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,160,300 B2 | 1/2007 | Jackson |
| 7,179,225 B2 | 2/2007 | Shluzas et al. |
| 7,179,261 B2 | 2/2007 | Sicvol et al. |
| 7,188,626 B2 | 3/2007 | Foley et al. |
| 7,250,052 B2 | 7/2007 | Landry et al. |
| 7,470,279 B2 * | 12/2008 | Jackson ............ 606/300 |
| 7,491,208 B2 * | 2/2009 | Pond et al. ............ 606/104 |
| 2002/0013585 A1 | 1/2002 | Gournay et al. |
| 2002/0020255 A1 | 2/2002 | Simon et al. |
| 2002/0116006 A1 | 8/2002 | Cohen |
| 2002/0193802 A1 | 12/2002 | Zdeblick et al. |
| 2003/0023240 A1 | 1/2003 | Amrein et al. |
| 2003/0040752 A1 | 2/2003 | Kitchens |
| 2003/0073998 A1 | 4/2003 | Pagliuca et al. |
| 2003/0135220 A1 | 7/2003 | Cauthen |
| 2003/0149341 A1 | 8/2003 | Clifton |
| 2003/0191371 A1 | 10/2003 | Smith et al. |
| 2003/0199872 A1 | 10/2003 | Markworth et al. |
| 2003/0208203 A1 | 11/2003 | Lim et al. |
| 2003/0216768 A1 | 11/2003 | Gitis et al. |
| 2003/0225408 A1 | 12/2003 | Nichols et al. |
| 2003/0236447 A1 | 12/2003 | Ritland |
| 2004/0002629 A1 | 1/2004 | Branch et al. |
| 2004/0024398 A1 | 2/2004 | Hovda et al. |
| 2004/0034351 A1 | 2/2004 | Sherman et al. |
| 2004/0039384 A1 | 2/2004 | Boehm, Jr. et al. |
| 2004/0138662 A1 | 7/2004 | Landry et al. |
| 2004/0143265 A1 | 7/2004 | Landry et al. |
| 2004/0144668 A1 | 7/2004 | Marshall et al. |
| 2004/0147928 A1 | 7/2004 | Landry et al. |
| 2004/0147937 A1 | 7/2004 | Dunbar, Jr. et al. |
| 2004/0172022 A1 | 9/2004 | Landry et al. |
| 2004/0176763 A1 | 9/2004 | Foley et al. |
| 2004/0215190 A1 | 10/2004 | Nguyen et al. |
| 2004/0267275 A1 | 12/2004 | Cournoyer et al. |
| 2005/0004593 A1 | 1/2005 | Simonson |
| 2005/0021031 A1 | 1/2005 | Foley et al. |
| 2005/0038432 A1 | 2/2005 | Shaolian et al. |
| 2005/0065517 A1 | 3/2005 | Chin |
| 2005/0070765 A1 | 3/2005 | Abdelgany et al. |
| 2005/0080418 A1 | 4/2005 | Simonson et al. |
| 2005/0085813 A1 * | 4/2005 | Spitler et al. ............ 606/61 |
| 2005/0090824 A1 | 4/2005 | Shluzas et al. |
| 2005/0131408 A1 * | 6/2005 | Sicvol et al. ............ 606/61 |
| 2005/0131419 A1 | 6/2005 | McCord et al. |
| 2005/0131420 A1 | 6/2005 | Techiera et al. |
| 2005/0131421 A1 * | 6/2005 | Anderson et al. ............ 606/99 |
| 2005/0131422 A1 | 6/2005 | Anderson et al. |
| 2005/0137593 A1 | 6/2005 | Gray et al. |
| 2005/0154389 A1 * | 7/2005 | Selover et al. ............ 606/61 |
| 2005/0159650 A1 | 7/2005 | Raymond et al. |
| 2005/0171540 A1 | 8/2005 | Foley et al. |
| 2005/0192570 A1 | 9/2005 | Jackson |
| 2005/0192579 A1 | 9/2005 | Jackson |
| 2005/0192589 A1 | 9/2005 | Raymond et al. |
| 2005/0215999 A1 * | 9/2005 | Birkmeyer et al. ............ 606/61 |
| 2005/0228380 A1 | 10/2005 | Moore et al. |
| 2005/0228392 A1 | 10/2005 | Keyer |
| 2005/0228400 A1 | 10/2005 | Chao et al. |
| 2005/0234449 A1 | 10/2005 | Aferzon |
| 2006/0009780 A1 | 1/2006 | Foley et al. |
| 2006/0025768 A1 | 2/2006 | Iott et al. |
| 2006/0036244 A1 | 2/2006 | Spitler et al. |
| 2006/0036255 A1 | 2/2006 | Pond, Jr. et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0074445 A1 | 4/2006 | Gerber et al. |
| 2006/0079894 A1 | 4/2006 | Colleran et al. |
| 2006/0079909 A1 | 4/2006 | Runco et al. |
| 2006/0084993 A1 | 4/2006 | Landry et al. |
| 2006/0106380 A1 | 5/2006 | Colleran et al. |
| 2006/0106394 A1 | 5/2006 | Colleran |
| 2006/0111712 A1 | 5/2006 | Jackson |
| 2006/0111714 A1 | 5/2006 | Foley et al. |
| 2006/0111715 A1 | 5/2006 | Jackson |
| 2006/0122597 A1 | 6/2006 | Jones et al. |
| 2006/0142761 A1 | 6/2006 | Landry et al. |
| 2006/0155278 A1 | 7/2006 | Warnick |
| 2006/0167454 A1 | 7/2006 | Ludwig et al. |
| 2006/0184178 A1 | 8/2006 | Jackson |
| 2006/0200135 A1 | 9/2006 | Sherman et al. |
| 2006/0229614 A1 | 10/2006 | Foley et al. |
| 2006/0241649 A1 | 10/2006 | Vasta et al. |
| 2006/0247630 A1 * | 11/2006 | Iott et al. ............ 606/61 |
| 2006/0247658 A1 | 11/2006 | Pond, Jr. et al. |
| 2006/0264962 A1 | 11/2006 | Chin et al. |
| 2006/0276803 A1 | 12/2006 | Salerni |
| 2006/0293680 A1 | 12/2006 | Jackson |
| 2006/0293693 A1 | 12/2006 | Farr et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0032162 A1 | 2/2007 | Jackson |
| 2007/0043357 A1 | 2/2007 | Kirschman |
| 2007/0043376 A1 | 2/2007 | Leatherbury et al. |
| 2007/0055242 A1 | 3/2007 | Bailly |
| 2007/0129731 A1 | 6/2007 | Sicvol et al. |
| 2007/0162009 A1 * | 7/2007 | Chao et al. ............ 606/61 |

FOREIGN PATENT DOCUMENTS

| | | |
|---|---|---|
| DE | 19726754 | 2/1999 |
| DE | 10027988 | 1/2002 |
| EP | 0528177 | 2/1993 |
| FR | 2 757 761 | 12/1996 |
| JP | 11076247 | 3/1999 |
| WO | WO 03/024949 A1 | 3/2003 |

OTHER PUBLICATIONS

Kevin T. Foley, M.D., CD Horizon® Sextant™: Rod Insertion System Surgical Technique,: Medtronic Sofamor Danek (2002).

(56) References Cited

OTHER PUBLICATIONS

Charles L. Branch, Jr., M.D., Kevin T. Foley, M.D., "Tangent™: Posterior Impacted Instrument Set Technique," Medtronic Sofamor Danek (2002).

Donald L. Hilton, Jr., M.D., Sylvain Palmer, M.D., "METRx: Microdiscectomy Surgical Technique," Medtronic Sofamor Danek (2001).

Atavi™: Atraumatic Spine Fusion System-Endoscopic Posterolateral Fusion, Endius (2001).

Aperture™ Spinal Access System, DePuy AcroMed (2003).

Thongtrangan, M.D., et al., "Minimally invasive spinal surgery: a historical perspective," Neurosurg Focus 16 (1): Aug. 13, 2004.

Mueller, M.D., et al., "A Keyhole Approach for Endoscopically Assisted Pedicle Screw Fiaxation in Lumbar Spine Instability," Neurosurgery, vol. 47, No. 1, Jul. 2000.

Turner, M.D., "A New, Radially Expanding Access System . . .", The Journal of the American Association of Gynecologic Laparoscopists, vol. 3, No. 4, Aug. 1996.

Kambin, M.D., "The Role of Minimally Invasive Surgery in Spinal Disorders", Advances in Operative Orthopedics, vol. 3, 1995.

Stryker Spine, Technique Guide, XIA Spinal System, dated 1999.

DePuy Acromed, Technique Guide, Moss Miami System, dated 1998.

DePuy Viper 2, Technique Guide, dated 1998.

* cited by examiner

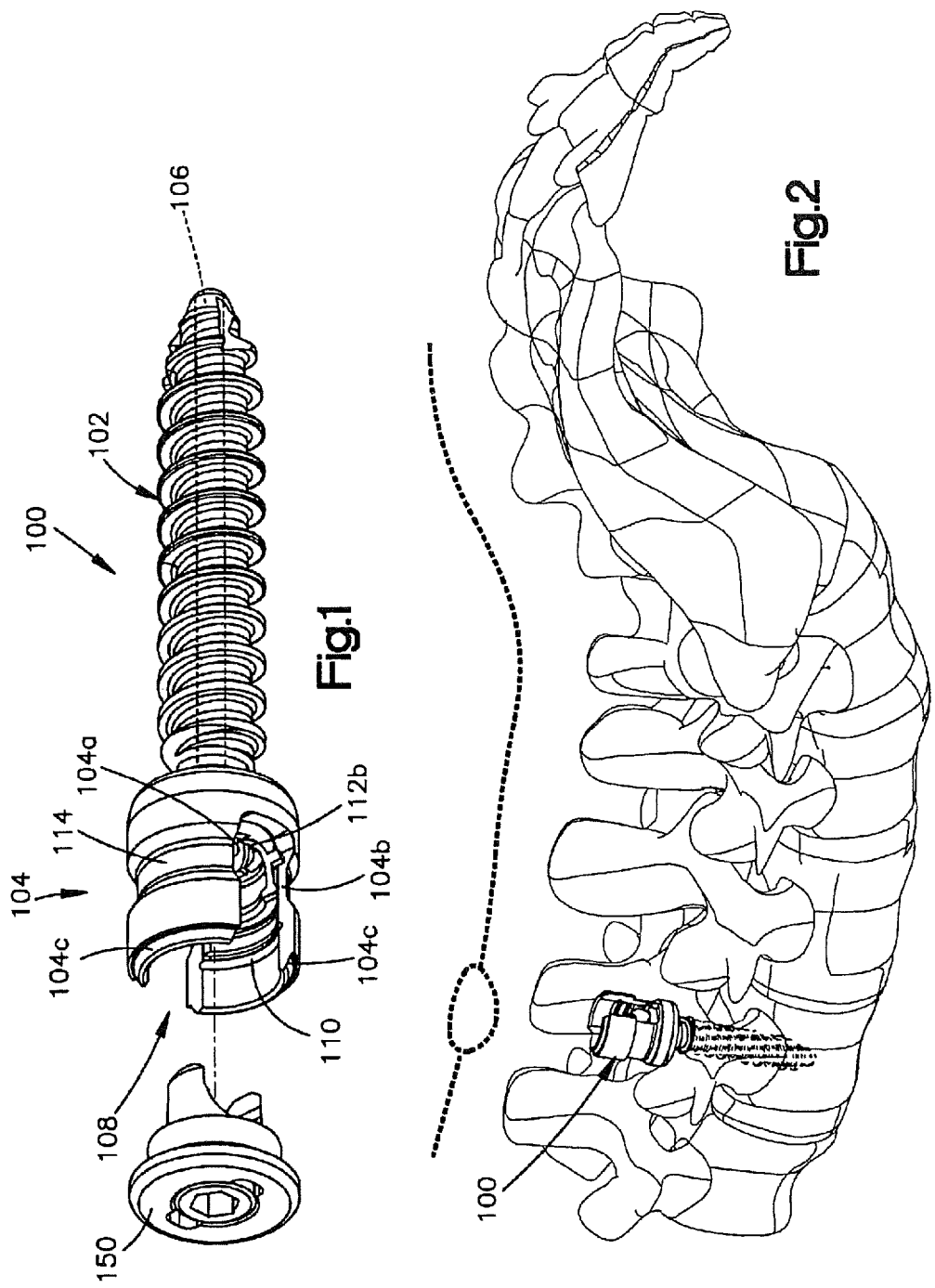

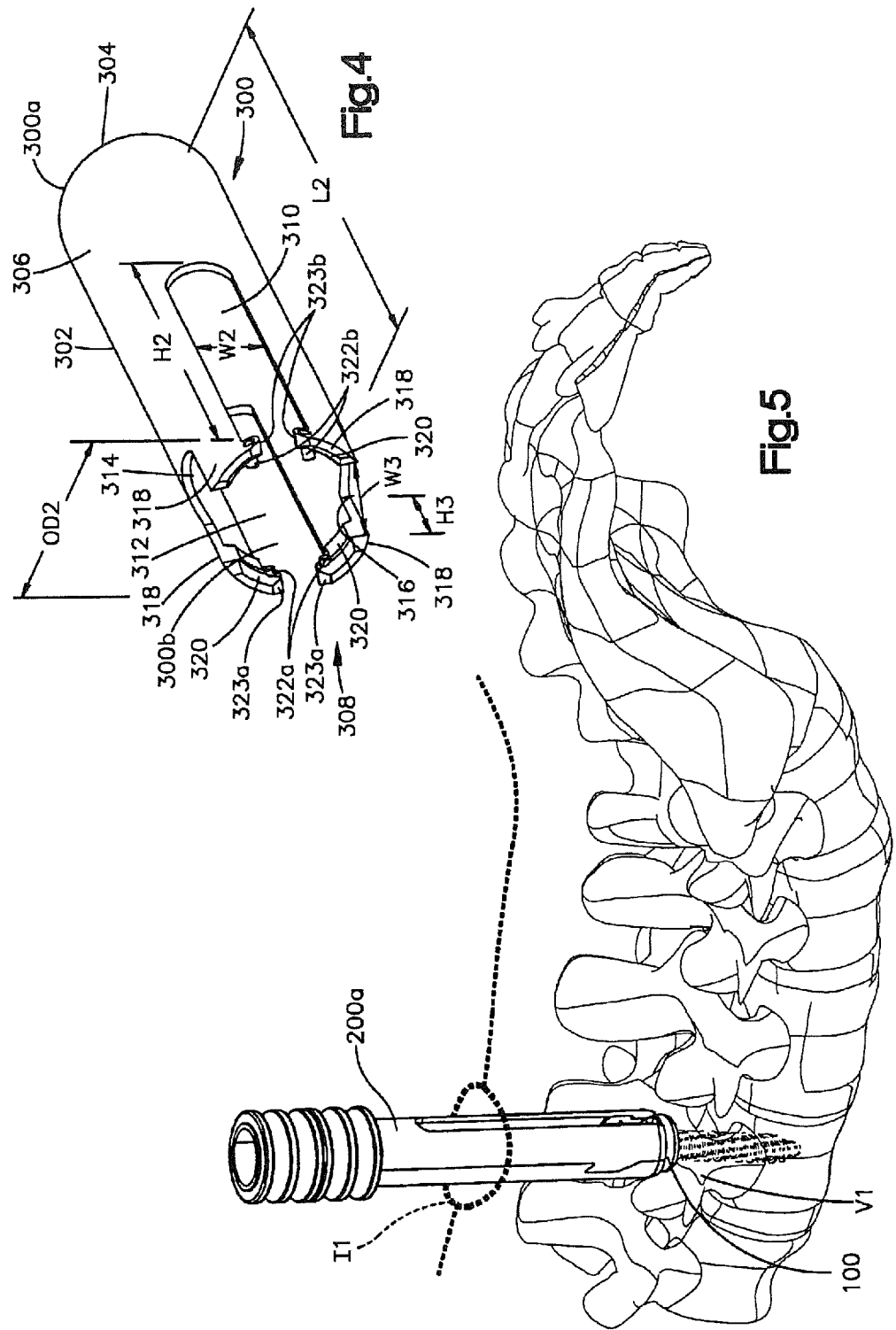

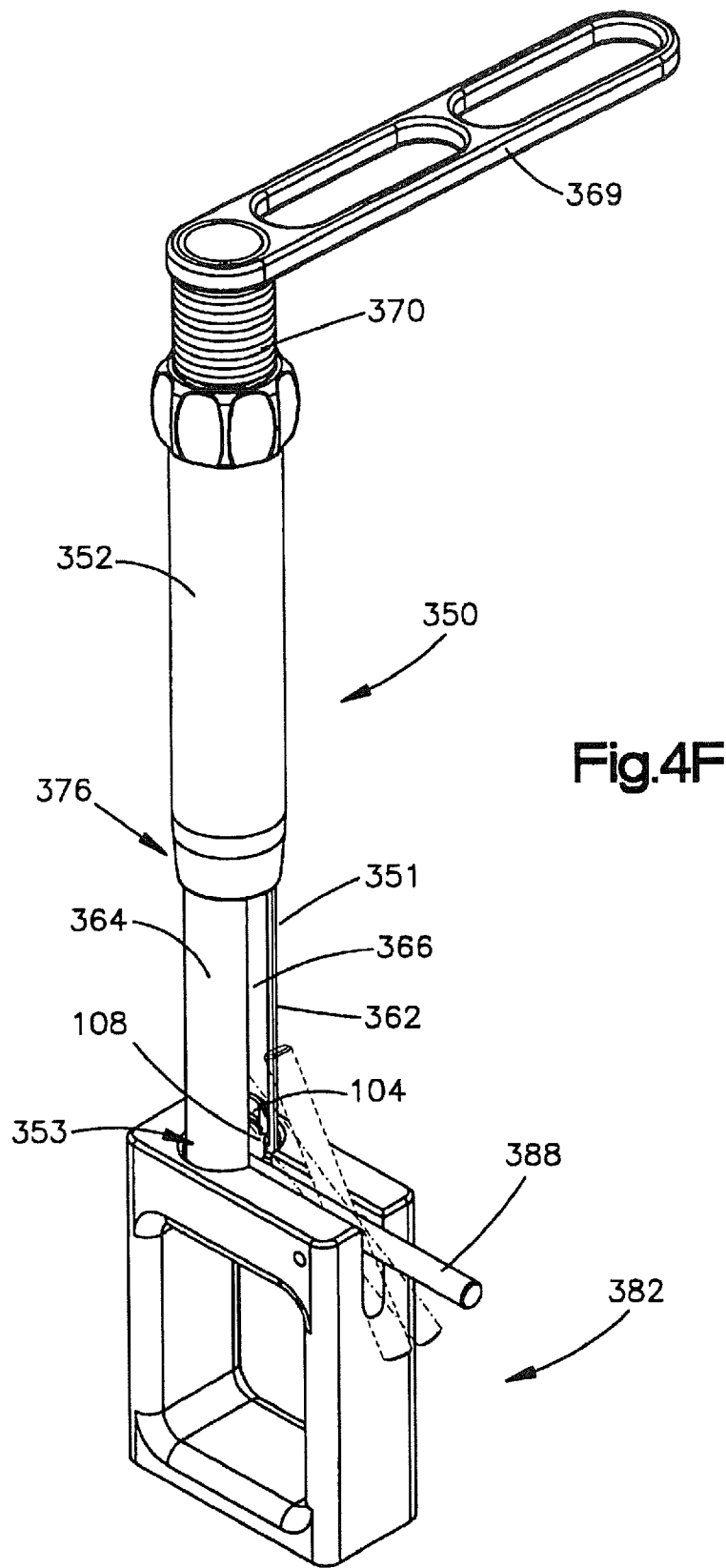

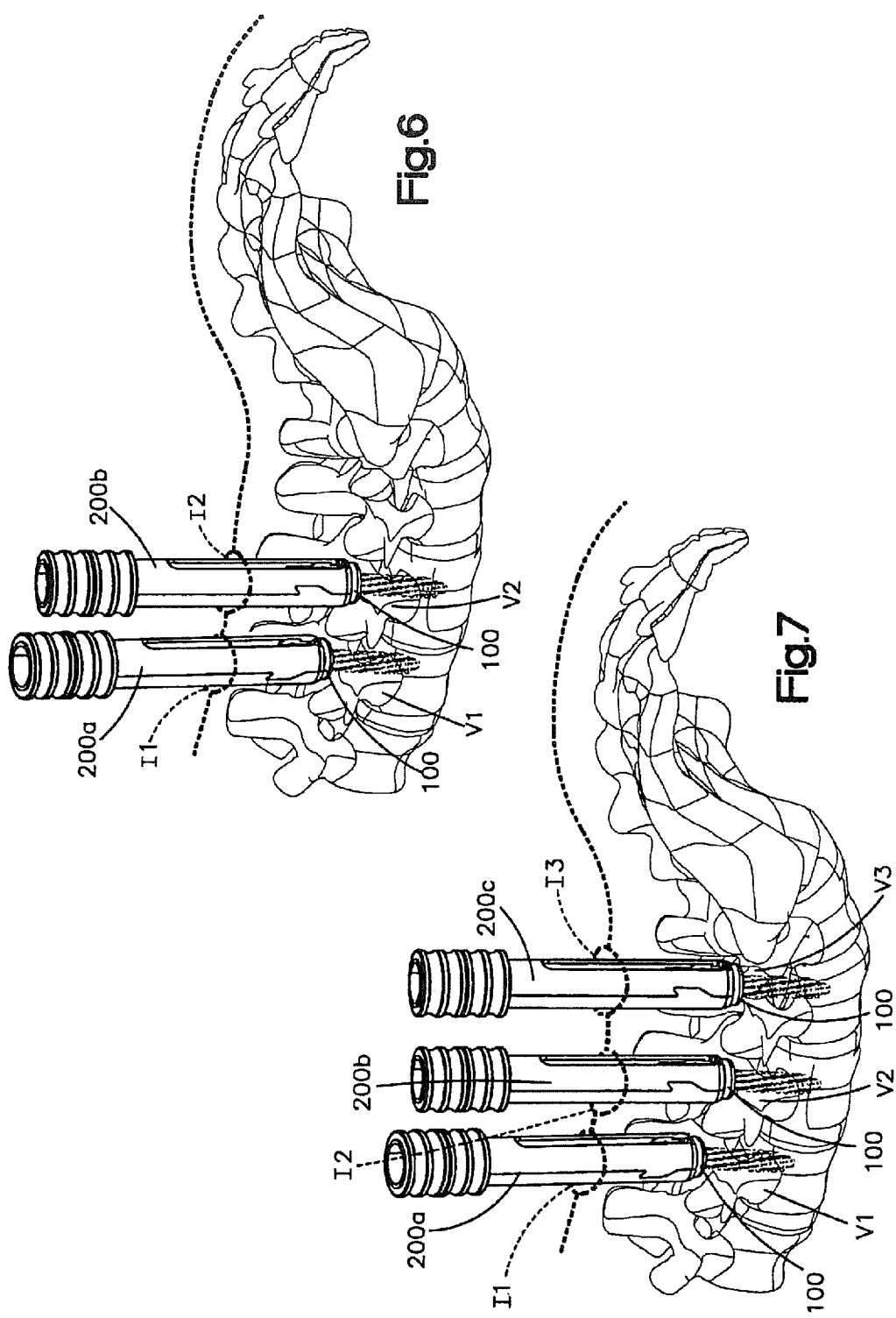

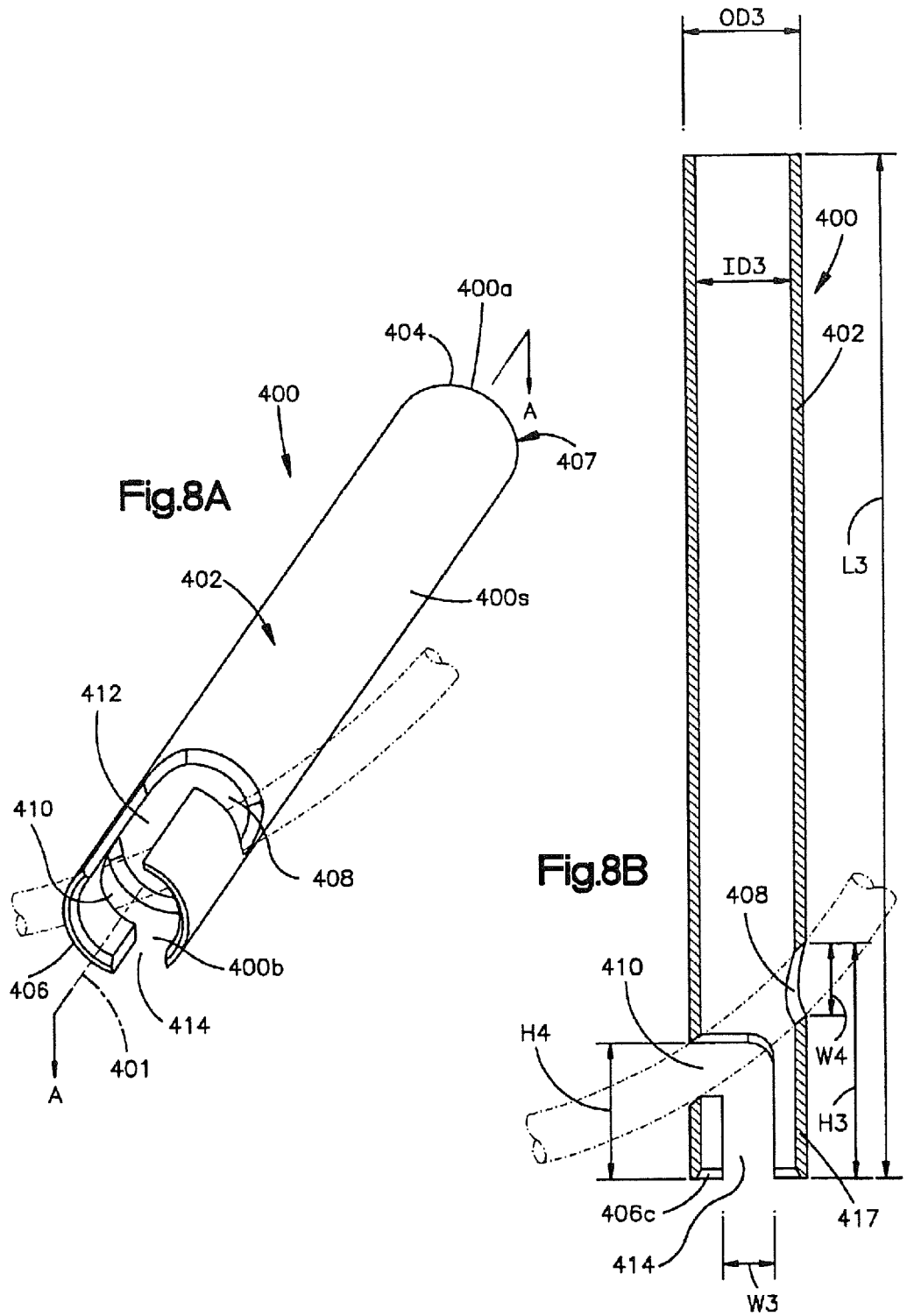

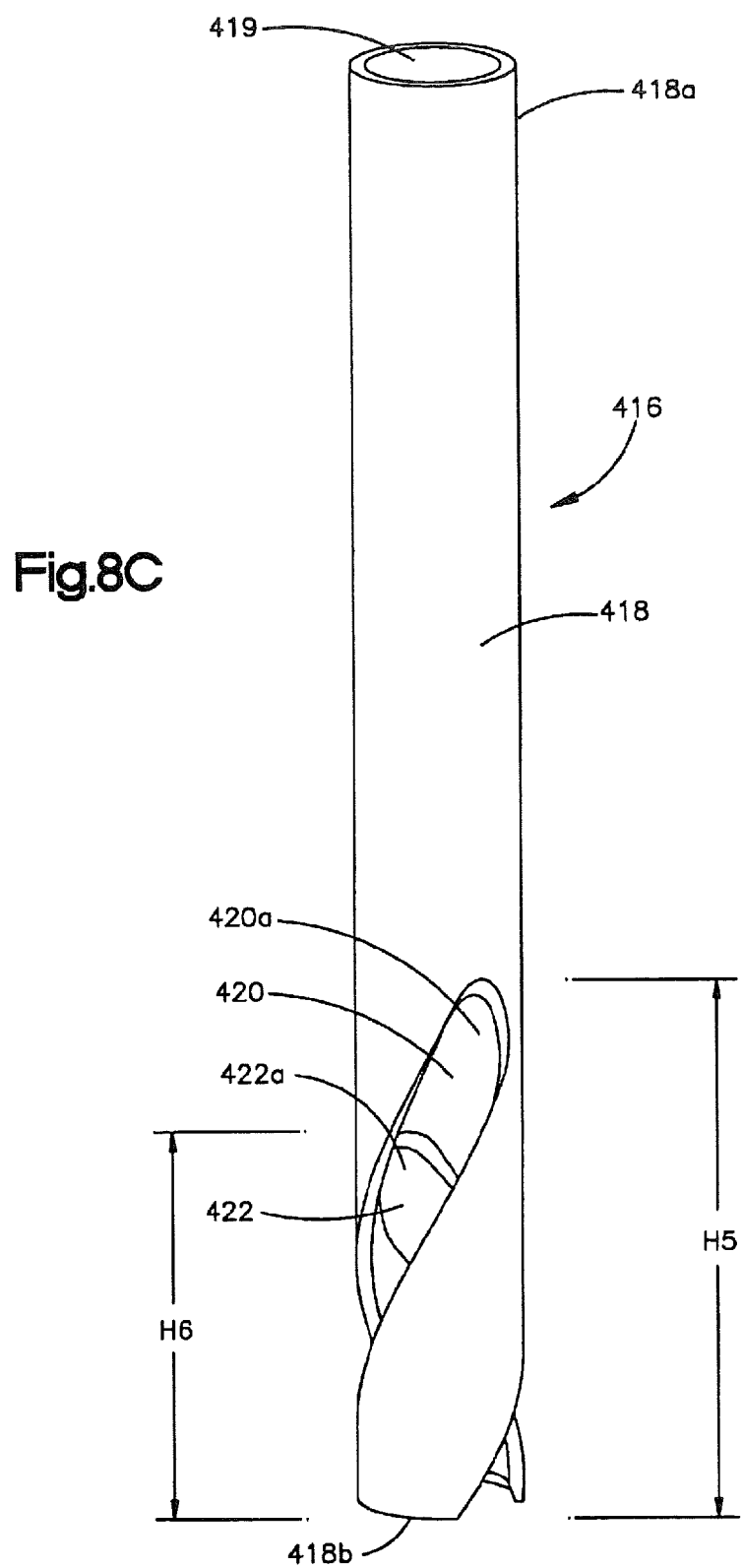

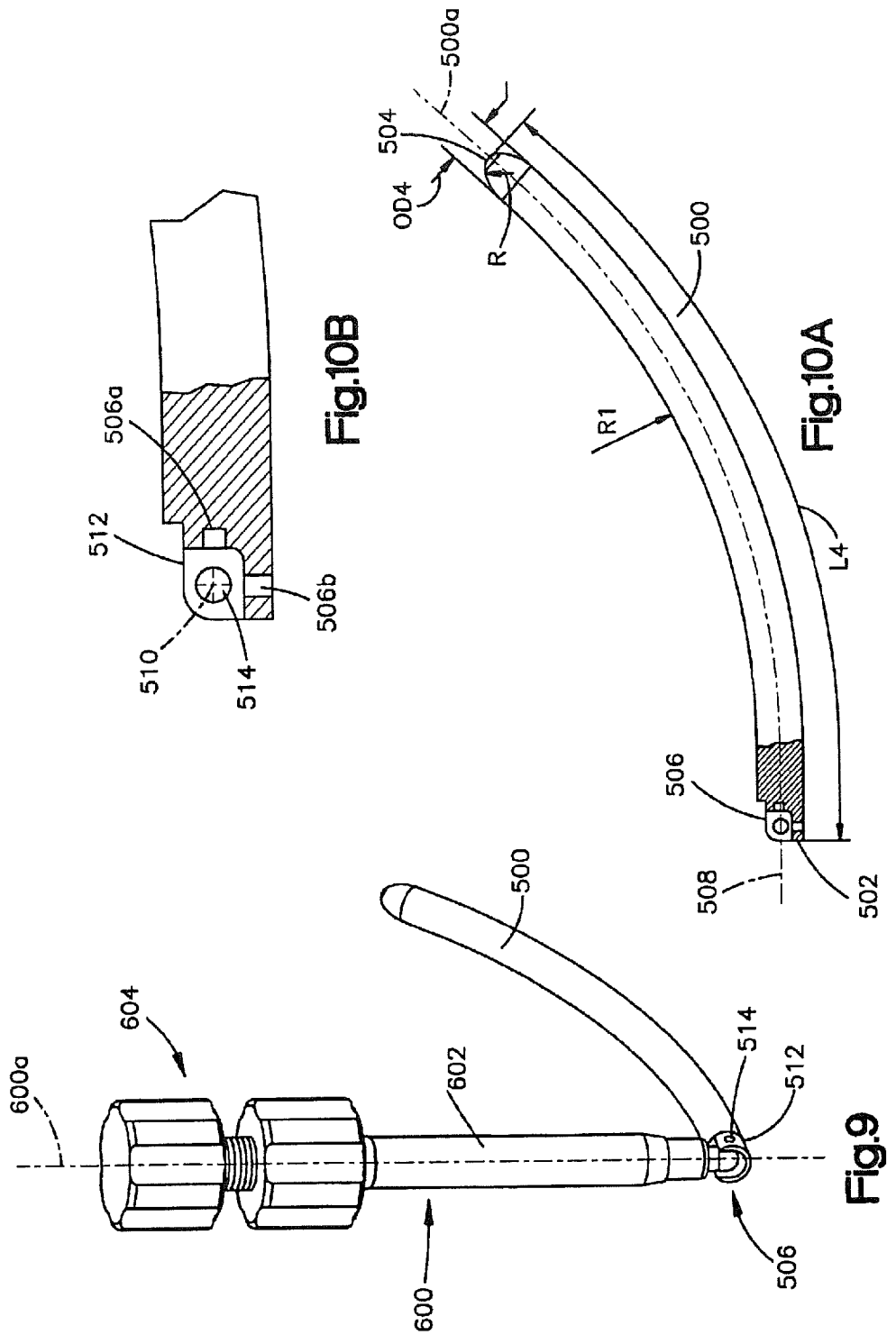

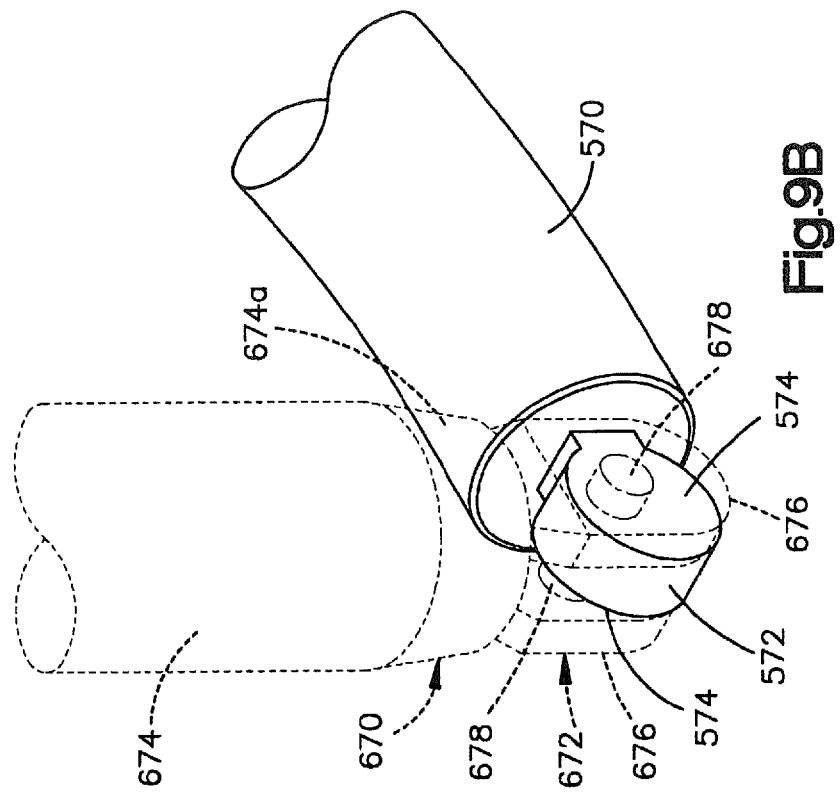
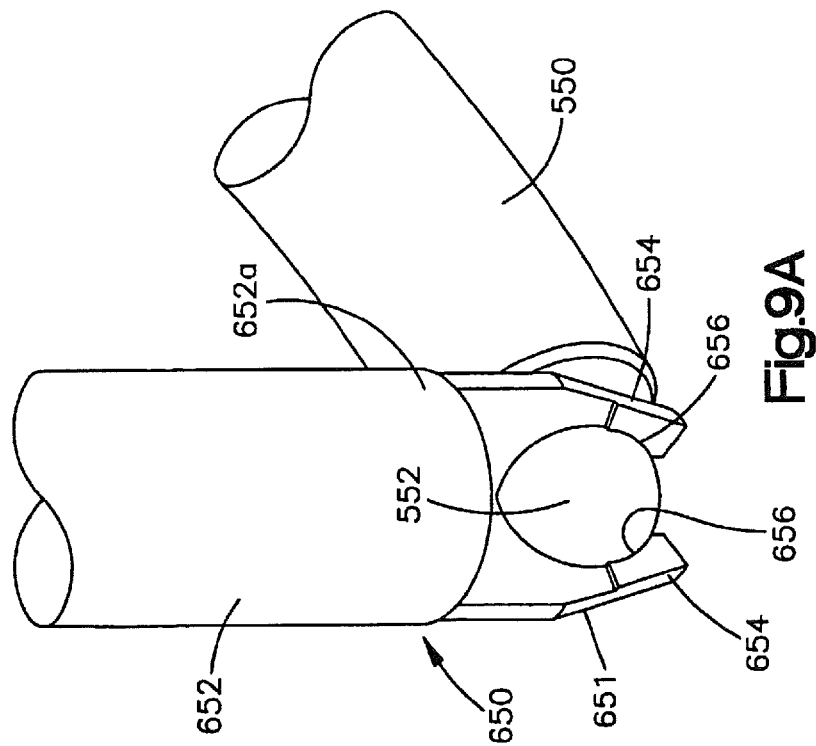

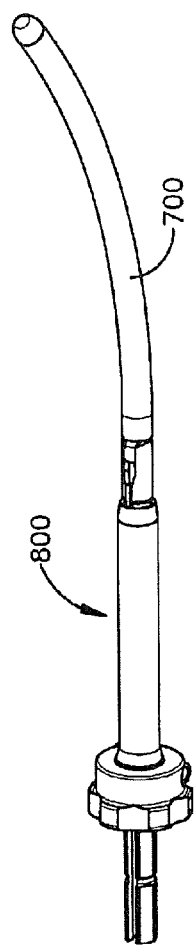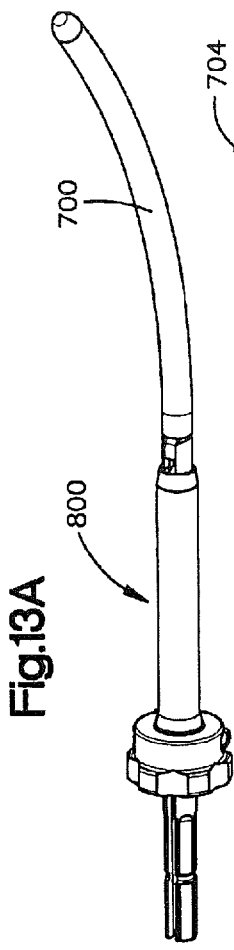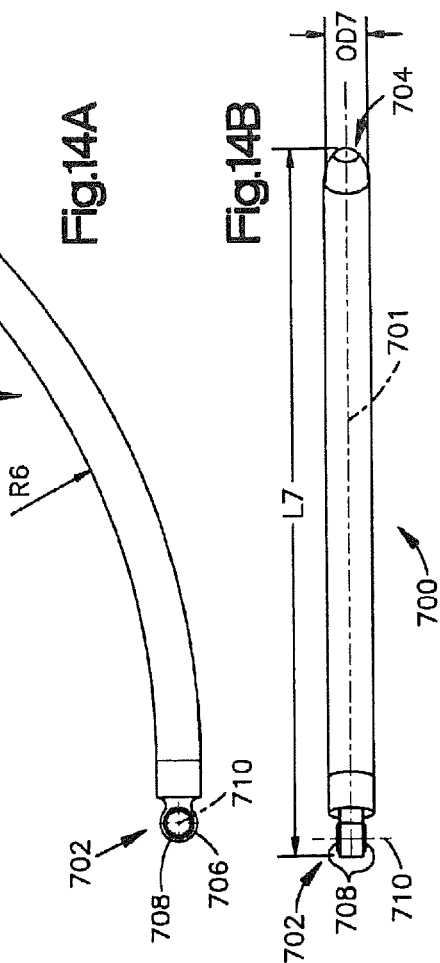
Fig.13A
Fig.13B
Fig.14A
Fig.14B

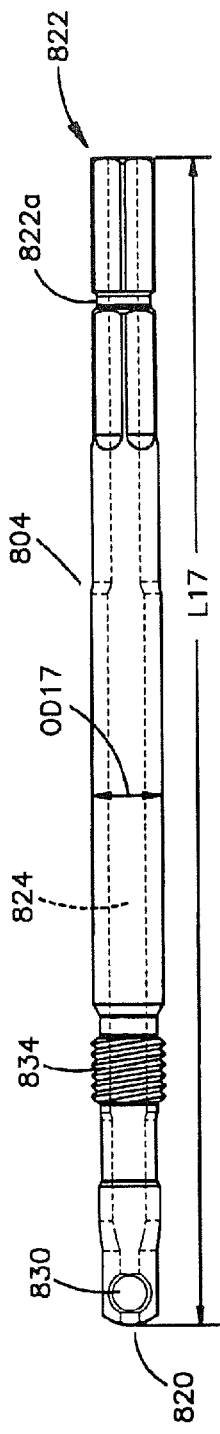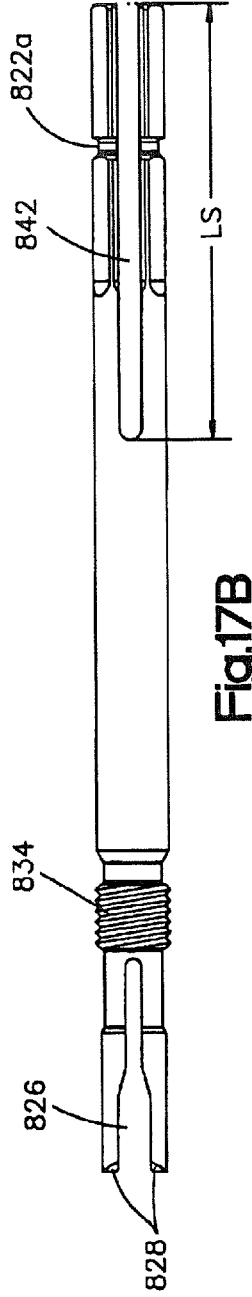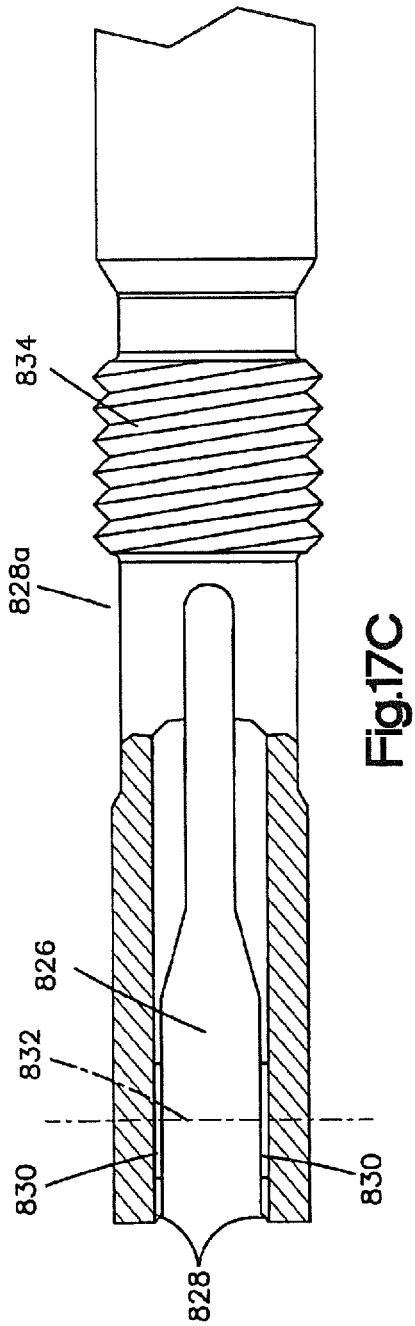
Fig.17A
Fig.17B
Fig.17C

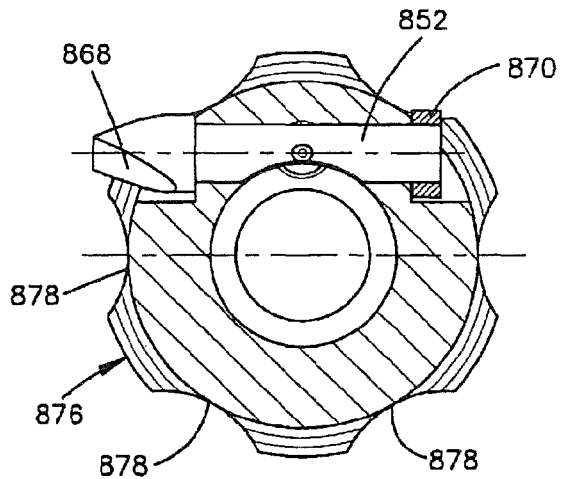
Fig.19A
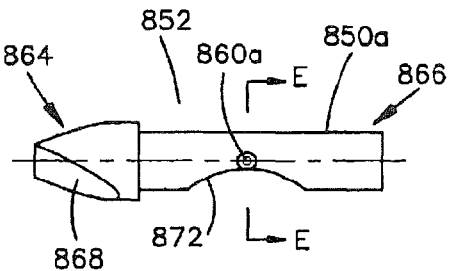
Fig.19B
Fig.19C
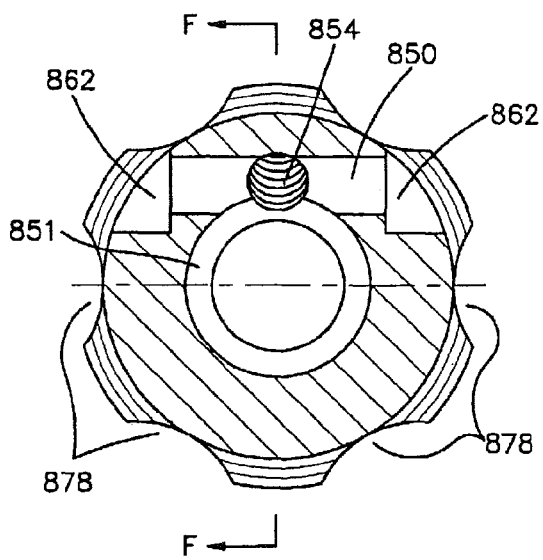
Fig.19D
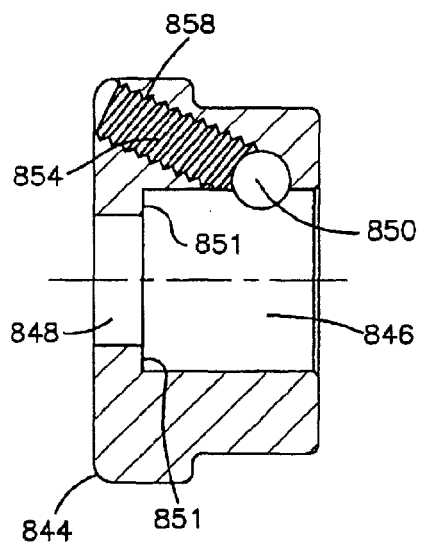
Fig.19E

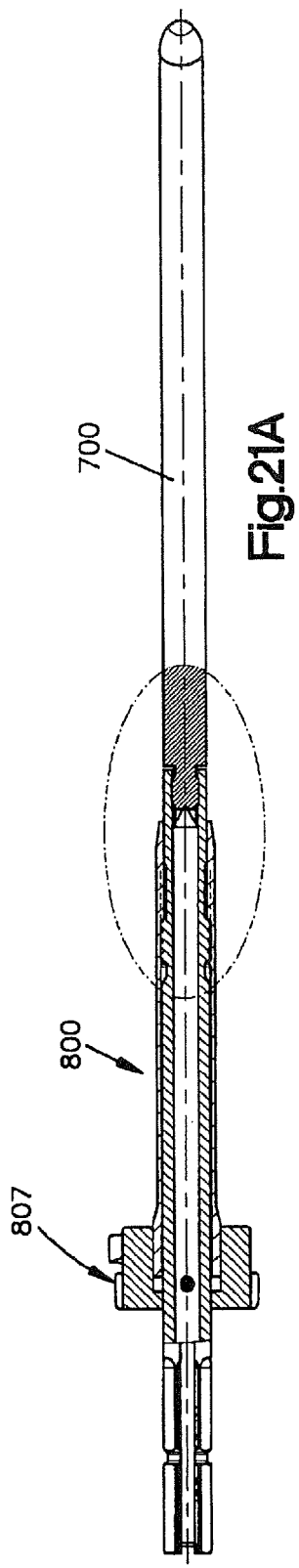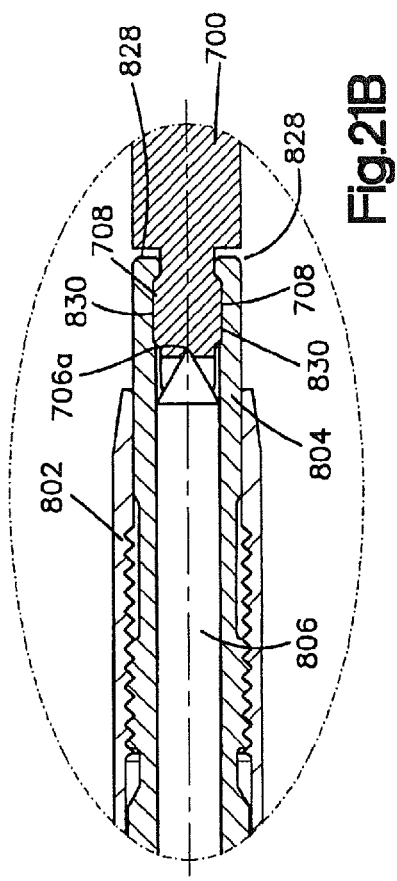

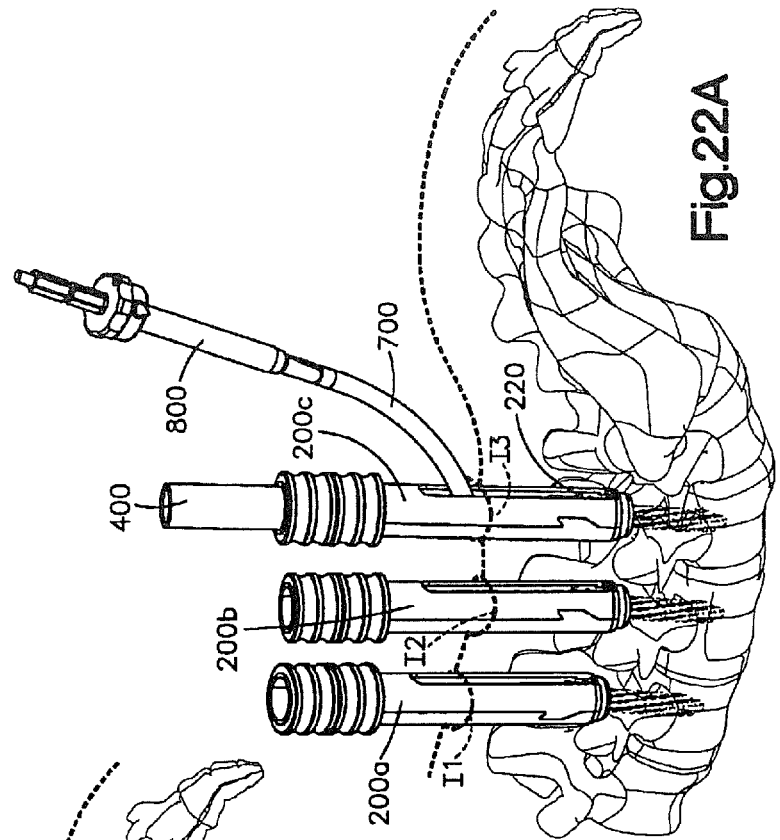
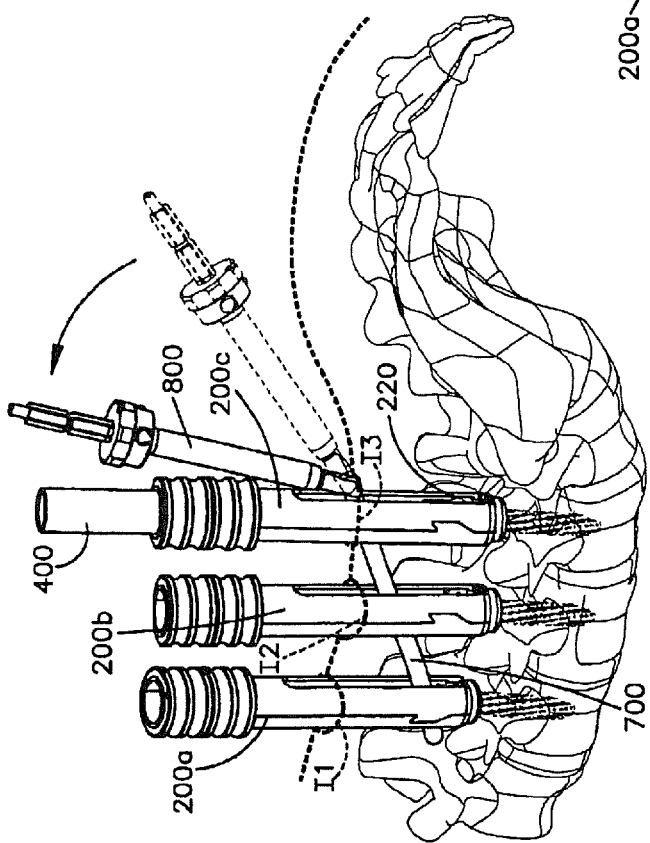

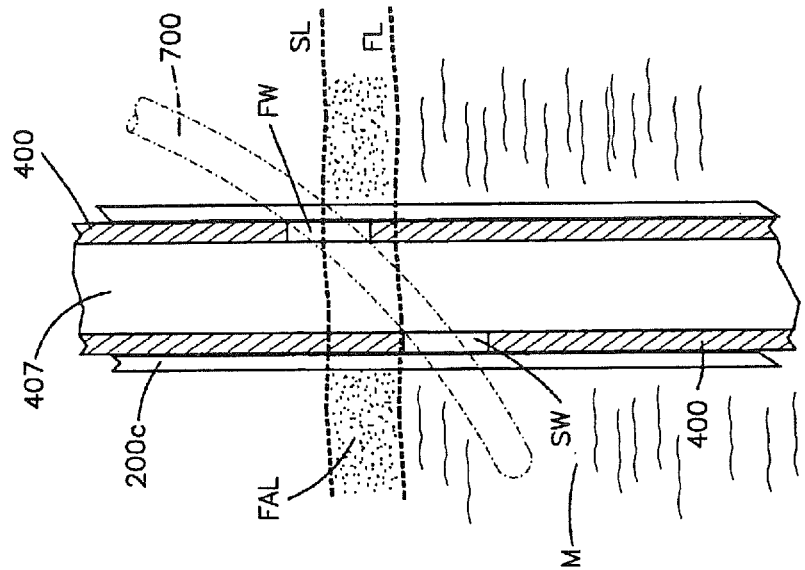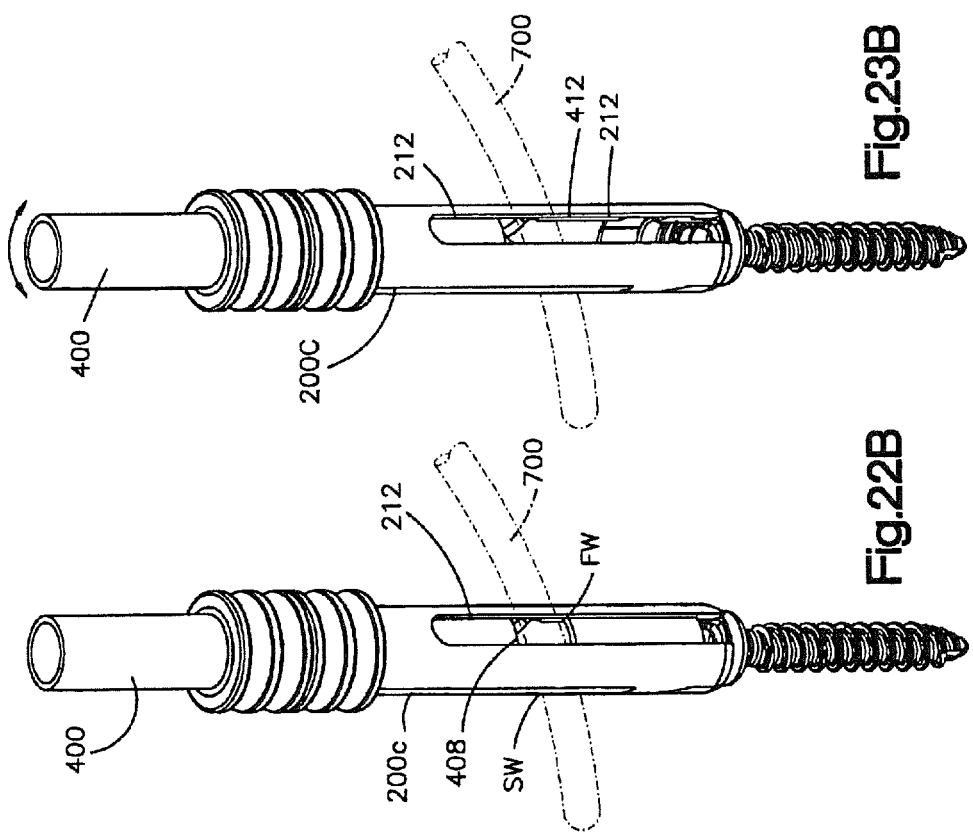

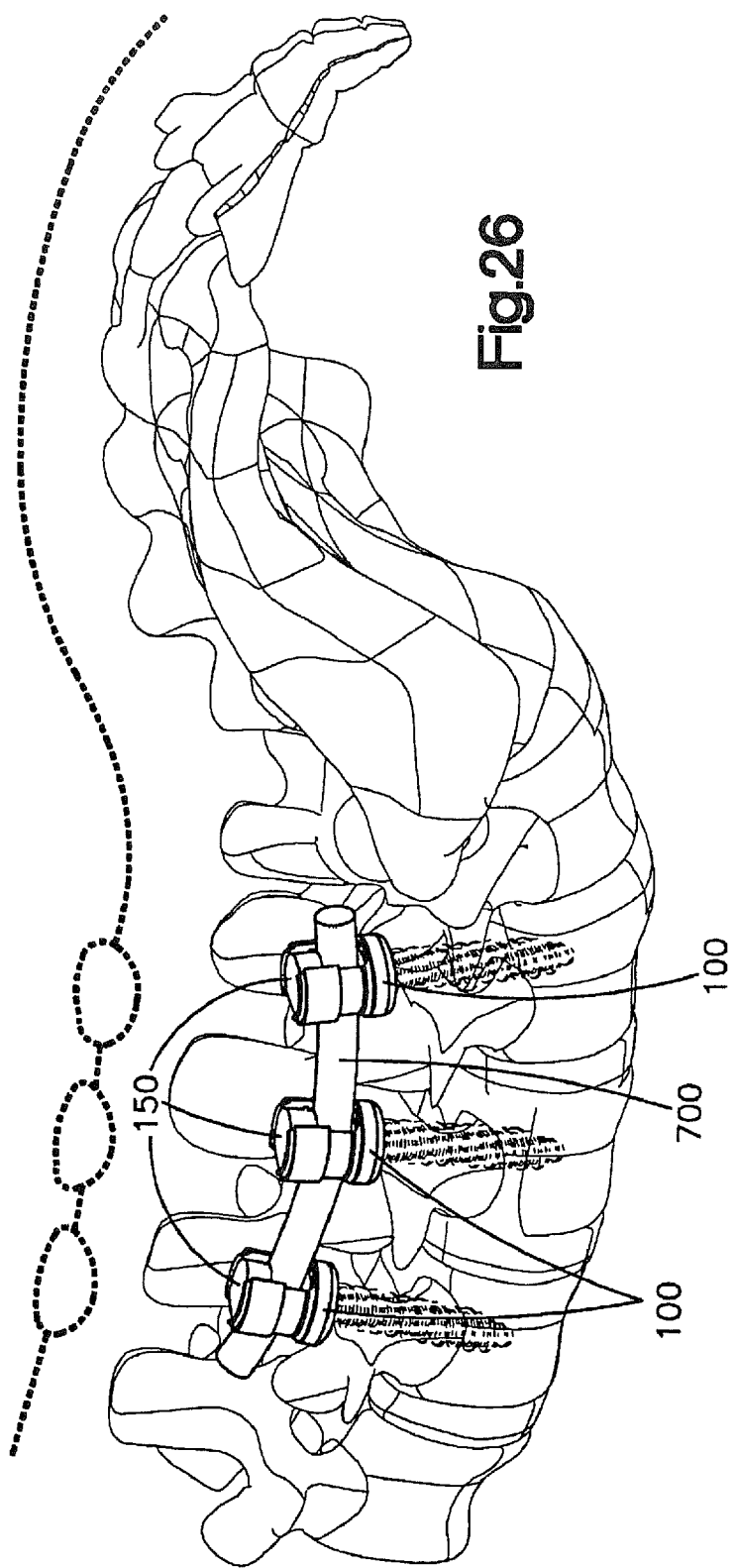

METHODS OF SPINAL FIXATION AND INSTRUMENTATION

CROSS-REFERENCE TO RELATED APPLICATIONS

The present application is a continuation of U.S. patent application Ser. No. 11/213,041, filed Aug. 25, 2005 U.S. Pat. No. 7,909,830, entitled "METHODS OF SPINAL FIXATION AND INSTRUMENTATION", the entire disclosure of this application is incorporated herein by reference.

FIELD OF THE INVENTION

The present invention is directed to methods of spinal fixation and, in particular, surgical instruments for performing a minimally invasive spinal fixation procedure.

BACKGROUND OF THE INVENTION

Spinal fixation systems which are used to correct spinal deformities and treat spinal degenerations generally consist of a series of bone fasteners anchored in, for example, the pedicle of adjacent vertebra. The bone fasteners are interconnected to one another by one or more elongated spinal rods or plates. In order to access the spinal area for implantation of these spinal fixation systems and their individual components, open approach surgical techniques have traditionally been employed. These open procedures generally involve large skin incisions and extensive tissue retraction and resection, all which may result in considerable post-operative pain and prolonged recovery time.

More recently, surgeons have used minimally invasive techniques to reduce the post-operative effects of spinal fixation procedures. A paraspinal approach is one form of minimally invasive technique and involves muscle splitting or muscle sparing in order to gain access to the posterior elements of the spine. Such a technique minimizes trauma to tissues adjacent the spine. Unlike open approaches where muscles and other soft tissue are cut, split, stripped and dissected, the paraspinal approach involves separation or splitting of the muscles along their fibers. To perform a paraspinal surgical procedure, a midline skin incision is made and followed by bi/unilateral fascia incision. The muscles are then separated to allow access to the spine via a single skin incision. Additionally, one or more off-midline skin incisions may be made to allow for a more direct approach.

Implanting a spinal rod fixation system generally involves at least two steps: (i) placing implants (e.g., screws) into the spine and (ii) inserting a rod between the implants. The starting insertion point, the trajectory of the implants and the implants' size are important to proper implant placement. The spinal implant generally comprises a screw portion and a body portion. The screw portion is inserted into the spine and the body portion generally has a channel into which a spinal rod is inserted and secured. The procedure to insert the rod may require insertion of the rod through an incision in the skin, which may be separate and distinct from the incision through which the implant(s) is placed. In other procedures, the rod is inserted through the same incision as the implant(s).

It is desirable to have a minimally invasive spinal implant and rod introduction system which minimizes trauma to the body, enables a rod to be readily connected to multiple implants anchored at varying depths in the body, is generally simple to use and enhances direct visualization of the rod as the rod is inserted into spinal implants.

SUMMARY OF THE INVENTION

The present invention relates to a method of performing a fixation procedure and the instrumentation used to perform the procedure. A radiographic image may be taken of the spine, including the vertebrae which are to receive implants. From the radiographic image, one or more insertion points may be located on a patient's back. A surgeon may make one or more incisions in a patient's back to form one or more openings. Thereafter, a surgeon may form a passageway through the incision(s) from the skin to the spine (e.g., by dilation or palpation). An entire procedure may be performed through a single incision or a procedure may be performed using multiple incisions.

A screw may be inserted through the incision. The screw may have a shaft, which may be inserted into bone, and a head portion operably connected to the shaft, preferably so the head portion can move relative to the screw shaft and preferably polyaxially rotate relative to the screw shaft. A drill, awl, probe and/or screwdriver may be used to insert the screw into a vertebrae. An insertion guide may be attached to the screw and, in particular, the head portion of the screw before or after the screw has been inserted into the body.

In one embodiment, the insertion guide may have a first and second section which may be connected to each other to form a tube having a bore therethrough. The first section may have a distal end, a proximal end, a first longitudinal slot extending from the distal end towards the proximal end, and at least one protrusion. The second section may have a distal end, a proximal end, a second longitudinal slot extending from the distal end towards the proximal end, and at least one recess for receiving the at least one protrusion. In the assembled condition, the second longitudinal slot may be diametrically opposed to the first longitudinal slot. Moreover, the distal ends of the first and second sections may be sized and configured to engage the head portion of a screw. For example, the distal end of at least one of the first and second sections may have a flange and at least one retaining portion extending from the flange into the bore. The flange may be sized and configured to be inserted into a groove in the head portion of the screw to prevent the screw and the insertion guide from being separated from each other. The at least one retaining portion may be sized and configured to engage at least one surface of the head portion of the screw to prevent rotation of the insertion guide with respect to the screw. Furthermore, at least one of the first and second sections may have a ring member which may provide a gripping surface for a surgeon to connect and/or disconnect the first and second sections.

In another embodiment, the insertion guide may have an elongated body with a distal end, a proximal end, and a bore extending from the distal end to the proximal end. The body may have first and second longitudinal slots which may extend from the distal end towards the proximal end of the insertion guide. The first and second longitudinal slots may be diametrically opposed to each other. At least one slot may be positioned between the first and second longitudinal slots. Such a construction may form a plurality of arms. The arms may engage the head portion of the screw. The plurality of arms may have a flange and at least one retaining portion extending from the flange into the bore. The flange may be sized and configured to be inserted into a groove in the head portion of the screw to prevent the screw and insertion guide from being separated from each other. The at least one retaining portion may be sized and configured to engage at least one surface of the head portion of the screw to prevent rotation of the insertion guide with respect to the screw.

In yet another embodiment, the insertion guide may have an inner sleeve and an outer sleeve. The inner sleeve may comprise a distal end, a proximal end, a bore extending from the distal end to the proximal end, a body, first and second arms extending from the body, first and second longitudinal slots positioned between the arms, and an actuating mechanism positioned along the body. The outer sleeve may comprise a distal end, a proximal end and an engagement member. Moreover, the outer sleeve may have a first position where the proximal end of the outer sleeve may be positioned a first distance from the proximal end of the inner sleeve and a second position where the proximal end of the outer sleeve may be positioned a second distance from the proximal end of the inner sleeve, wherein the second distance is greater than the first distance. The outer sleeve may be positioned over the inner sleeve so that the engagement member of the outer sleeve may engage the actuating mechanism of the inner sleeve for moving the outer sleeve between the first and second position.

One method of attaching an insertion guide to a screw may comprise providing a screw having a shaft and a head portion, wherein the head portion may have a channel therethrough, providing a holder comprising a body, an opening through the body for receiving the screw, a ledge and counterbore proximate the opening, and a fixing member, positioning the shaft of the screw through the opening so that the head portion is positioned against the ledge, moving the fixing member between a first position where the fixing member is not positioned within the channel of the head portion and a second position where at least a portion of the fixing member is positioned within the channel of the head portion, providing an insertion guide having a proximal end and a distal end, inserting the distal end of the insertion guide into the counterbore, and engaging the distal end of the insertion guide with the head portion of the screw.

In one method, the process of inserting a screw into a vertebrae and attaching an insertion guide to the screw may be repeated through additional, separate incisions. Once the desirable number of screw/insertion guide assemblies have been positioned in the body, a sleeve may be inserted through an outermost insertion guide (e.g., the insertion guide attached to a vertebrae at the end of the group of vertebrae to be connected). The sleeve may be an elongated body with a distal end, a proximal end, and a passageway extending from the distal end to the proximal end. The sleeve may have a first longitudinal opening which may extend a first distance from the distal end towards the proximal end and a second longitudinal opening diametrically opposed to the first longitudinal opening which may extend a second distance from the distal end towards the proximal end. The second distance may be less than the first distance. The sleeve may also have a first opening which may intersect the first longitudinal opening at an angle and a second opening which may intersect the second longitudinal opening at an angle. In one embodiment, the first opening may intersect the first longitudinal opening at a substantially perpendicular angle and the second opening may intersect the second longitudinal opening at a substantially perpendicular angle. The sleeve may be used to guide the movement of a rod through the insertion guides and tissue.

A rod may be inserted through the sleeve, through tissue and into the head portions of screws. In one embodiment, a surgeon may grab an end of the rod and insert it with his/her hand/fingers. In another embodiment, a holding instrument may be attached to the rod and may be used to insert the rod into the body. In a preferred embodiment, the rod may have an axis, a distal end, a proximal end, and a receiving portion at the proximal end. The holding instrument may have an axis and may comprise an outer member and an inner member. The outer member may have a distal end, a proximal end, a pair of flexible arms proximate the distal end, and a passageway extending from the proximal end to the distal end. The pair of arms may be positionable within the receiving portion of the rod. The inner member may have a distal end, a proximal end, and a tip at the proximal end. Moreover, the inner member may be sized and configured for insertion through the passageway of the outer member so that the distal end of the inner member may be inserted between the pair of arms. When the distal end of the inner member is inserted between the pair of arms, the arms may each move outward and engage the receiving portion of the rod. In one embodiment, the receiving portion of the rod may have at least one recess and the tip of the inner member may be positionable within that at least one recess. In this way, an operator may fix the orientation of the holding instrument relative to the rod. For example, in one orientation, the axis of the rod may be aligned with the axis of the holding instrument and, in another orientation, the axis of the rod may be at an angle with respect to the holding instrument. Furthermore, the outer member may have a threaded portion inside the passageway for engaging corresponding threads on the inner member such that rotation of the inner member relative to the outer member may results in the inner member moving into and out of the passageway of the outer member.

The receiving portion may also have one or more, preferably at least two or more bores or grooves. Each bore or groove may receive an arm of the outer member such that the rod may be rotated with respect to the holding instrument. When the distal portion of the inner member is inserted in between the arms, the arms may flex outwards and may engage the bores or grooves to hold the rod relative to the holding instrument. In one embodiment, each arm may have a hemispherical shaped portion and the grooves may be hemispherical in shape to receive the hemispherical shaped portion of the arms.

In another embodiment, the rod may have an axis, a distal end, a proximal end, and an engagement portion at the proximal end. The holding instrument may have an axis and may include an outer sleeve and an inner sleeve. The outer sleeve may have a distal end, a proximal end and a passageway therethrough. The inner sleeve may have a distal end and a proximal end, and may be positioned within the passageway of the outer sleeve. The inner sleeve may have a portion at the distal end for engaging the engagement portion of the elongated rod. The distal end of the outer sleeve may be selectively moveable over the distal end of the inner sleeve to fix the holding instrument with respect to the rod.

In some embodiments, the engagement portion of the elongated rod may be spherical in shape and the inner sleeve may have a plurality of arms at the distal end of the inner sleeve for engaging the engagement portion. Alternatively, the engagement portion of the elongated rod may have a plurality of flat surfaces and the inner sleeve may have at least two prongs at the distal end of the inner sleeve, wherein the at least two prongs may each have at least one pin. The at least one pin is made of a material which is harder than a material of the engagement portion of the elongated rod.

In another embodiment, the portion at the distal end of the inner sleeve may have at least two prongs, wherein each prong may each have a recess and the engagement portion may have at least one protrusion which may be inserted into a recess of a prong. In this way, the rod may be held with respect to the holding instrument so that the rod may rotate relative to the holding instrument. The inner sleeve may also have external threads which may be engaged by internal threads in the passageway of the outer sleeve such that rotation of the outer sleeve relative to the inner sleeve may result in movement of the outer sleeve along the axis of the holding instrument. In this way, the distal end of the outer sleeve may be selectively positioned over or disengaged from the distal end of the inner sleeve. When the distal end of the outer sleeve is positioned over the prongs of the inner sleeve, the rod may be translationally fixed with respect to the holding instrument (i.e., the rod may be prevented from being separated from the holding instrument) while still being able to rotate relative to the holding instrument.

In order to assist in fixing rotation of the rod with respect to the holding instrument, the holding instrument may be provided with an elongated member which may be positioned within the inner sleeve and moveable therein. The elongated member may have a distal end, a proximal end, a guide member and a taper portion at the distal end. The tapered portion/tip of the elongated member may have a point which may be inserted into a receiving portion in the engagement portion of the rod to hold the rod in place with respect to the holding instrument. The guide member may be inserted into at least one slot in the inner sleeve so that the elongated member may move along the axis of the holding instrument but may not rotate about the axis relative to the inner sleeve. The elongated member may be operably associated with the outer sleeve so that as the distal end of the outer sleeve moves further over the prongs of the inner sleeve, the elongated member may engage the rod, thereby fixing rotational movement of the rod with respect to the holding instrument.

In one embodiment, the rod and/or engagement portion of the rod may be made of a soft material (e.g., titanium) and the elongated member may be made of a harder material (e.g., stainless steel) such that when the elongated member engages the engagement portion of the rod, the tapered portion/tip of the elongated member may deform, dig-in or create a depression in the engagement member. Such a construction may create a step-less configuration (i.e., the rod and the holding instrument may be positioned at any angle relative to each other). In some embodiments, the engagement portion of the rod may have one or more receiving portions or recesses positioned at predetermined intervals along the engagement portion of the rod. Such a construction may result in a stepped configuration (i.e., the rod and holding instrument may be positioned at pre-set fixed angles relative to each other). In an embodiment where the engagement portion of the rod has only one recess, the recess may be positioned so that when the tapered portion/tip of the elongated member engages the recess, the axis of the rod may be aligned with the axis of the holding instrument.

The holding instrument may further comprises an actuation mechanism which may be used to move the outer sleeve and/or elongated member relative to the inner sleeve. The actuation mechanism may have a gripping surface to provide a surgeon with an enhanced grip. The actuation mechanism may have a first passageway which may have a first dimension. The first passageway may be sized and configured to receive the proximal end of the outer sleeve. The actuation mechanism may also comprise a second passageway which may have a second dimension which may be less than the first dimension. The inner sleeve and/or elongated member may be positioned through the second passageway. Such a construction may form a shoulder within the actuation mechanism. The guide member of the elongated member may be positioned between the shoulder of the actuation mechanism and the proximal end of the outer sleeve.

In order to hold the actuation mechanism to the outer sleeve, the actuation mechanism may be provide with a retaining member which may be rotatably received within a bore of the actuation mechanism. The retaining member may have a distal end, a proximal end, an outer surface, a knob at the proximal end and a notch in between the distal and the proximal ends. The outer sleeve may have a recess for selectively receiving the outer surface of the retaining member. When the outer surface of the retaining member is positioned in the recess of the outer sleeve, the outer sleeve may be fixed with respect to the retaining member and the actuation mechanism (e.g., the outer sleeve may be prevented from moving along the axis of the holding instrument and/or rotating about the axis of the holding instrument). The knob of the retaining member may be rotated so that the notch of the retaining member may face the recess of the outer sleeve. In such an orientation, the outer sleeve may be moveable relative to the retaining member and the actuation mechanism.

A holding member may be positioned through the actuation mechanism to fix the orientation of the retaining member within the actuation mechanism. The holding member may hold the retaining member in a first position, where the outer surface of the retaining member may be positioned in the recess of the outer sleeve (i.e., the outer sleeve may be locked in place with respect to the actuation mechanism), and a second position, where the notch may face the recess (i.e., the outer sleeve may be freely moveable respect to the actuation mechanism). In particular, the holding member may have a portion which may be inserted into at least one receiving portion of the retaining member.

Once a rod and holding instrument is selected by a surgeon, the rod may be inserted into the body. To insert the rod into the body, the sleeve may be initially positioned in an insertion guide so that the first and second openings of the sleeve may intersect the first and second longitudinal slots of the insertion guide, respectively, and, thus, may form a first and second window, respectively. The rod may be inserted through the incision in which the insertion guide and sleeve are located and may pass through the first and second windows, through tissue and through longitudinal slots of adjacent insertion guides. More particularly, the first window is preferably at least partially and, more preferably, entirely above the skin of the patient's back. The distal tip of the rod may be inserted and pushed through the first window above the patient's back and into the interior of the sleeve and insertion guide. The distal tip of the spinal rod may be further pushed so that it exits the second window, which is preferably positioned below the facia of the patient, and moves into muscle (e.g., the tissue layer below the facia). In an embodiment where the longitudinal slots of the insertion guide or openings/longitudinal openings of the sleeve do not form a first window above the skin level, the rod may be used to push down and move skin and fat layer out of the way. With the skin repositioned, the rod may be inserted through the longitudinal slots of the insertion guide and/or openings/longitudinal openings of the sleeve so that the rod is preferably inserted from above the patient's skin into the interior of the insertion guide and sleeve.

An operator may manipulate the insertions guides to align the longitudinal slots of the various insertion guides so that a rod may be inserted through the insertion guides. Once the rod has been positioned through a desired number of insertion guides, the sleeve may be rotated to a second position so that the first and second longitudinal openings of the sleeve may align with the first and second longitudinal slots of the insertion guide. The rod may then be slid down the longitudinal slots and openings and into the head portion (e.g., a U-shaped channel) of the screw. A surgeon may use the holding instrument to slide the rod down the longitudinal slots of the insertion guide. The holding instrument may be positioned through the same incision as the insertion guide containing the sleeve. With the rod in position in the head portion of the screws, the holding instrument may be disengaged from the rod and removed from the body. End caps may be inserted through the insertion guide and may be attached to the head portions of the screws so that the rod may be fixed between the end cap and a surface(s) of the head portion. After the rod has been locked in place, the insertion guides may be removed from the body. Alternatively, the end caps may be inserted after the insertion guides are removed from the body. With the insertion guides removed, the screws and rod form a fixation system. The incision(s) may be closed to complete the procedure.

BRIEF DESCRIPTION OF THE DRAWINGS

The methods of fixation and related instrumentation are explained in even greater detail in the following exemplary drawings. The method and its related instruments may be better understood by reference to the following drawings, wherein like references numerals represent like elements. The drawings are merely exemplary to illustrate the method and its related instruments, the structure and operation of the instruments and certain features that may be used singularly or in combination with other features and the invention should not be limited to the embodiments shown.

FIG. 1 is a perspective view of an exemplary embodiment of an implant for use with the present invention;

FIG. 2 is a perspective view of the spine with the implant of FIG. 1 inserted in a vertebrae;

FIG. 4 is a perspective view of an alternative exemplary embodiment of an insertion guide;

FIG. 4F is a perspective view of an exemplary embodiment of the holder of FIG. 4E being used with the insertion guide of FIG. 4A;

FIG. 5 is a perspective view the assembly of FIG. 3A attached to the spine;

FIG. 6 is a perspective view of a second assembly attached to the spine;

FIG. 7 is a perspective view of a third assembly attached to the spine;

FIG. 8A is a perspective view of an exemplary embodiment of a guide sleeve of the present invention;

FIG. 8B is a cross-sectional view of the guide sleeve of FIG. 8A along A-A;

FIG. 8C is a perspective view of an alternative exemplary embodiment of a guide sleeve of the present invention;

FIG. 9 is a perspective view of an exemplary embodiment of a fixation rod and holding instrument of the present invention;

FIG. 9A is a perspective view of an alternative exemplary embodiment of a fixation rod and holding instrument of the present invention;

FIG. 9B is a perspective view of another alternative exemplary embodiment of a fixation rod and holding instrument of the present invention;

FIG. 10A is a partial cross-sectional side view of the fixation rod of FIG. 9;

FIG. 10B is an enlarged view of the cross-section of FIG. 10A;

FIG. 13A is a perspective view of an alternative exemplary embodiment of a fixation rod and holding instrument of the present invention with the holding instrument in a first position;

FIG. 13B is a perspective view of the fixation rod and holding instrument of FIG. 13A with the holding instrument in a second position;

FIG. 14A is a side view of an exemplary embodiment of the fixation rod of FIGS. 13A and 13B;

FIG. 14B is a top view of the fixation rod of FIG. 14A;

FIG. 17A is a side view of an exemplary embodiment of an inner sleeve of the holding instrument of FIGS. 15A and 15B;

FIG. 17B is a top view of the inner sleeve of FIG. 17A;

FIG. 17C is an enlarged view of an end portion of the inner sleeve of FIG. 17B;

FIG. 19A is a cross-sectional view of an exemplary embodiment of an actuation mechanism of the holding instrument of FIG. 15A along D-D;

FIG. 19B is a side view of an exemplary embodiment of a retaining member of the actuation mechanism of FIG. 19A;

FIG. 19C is a cross-sectional view of the retaining member of FIG. 19B along E-E;

FIG. 19D is another cross-sectional view of the actuation mechanism of FIG. 15A along D-D without the retaining member;

FIG. 19E is a cross-sectional view of the actuation mechanism of FIG. 19D along F-F;

FIG. 21A is a partial cross-sectional top view of the fixation rod and holding instrument of FIG. 13B;

FIG. 21B is an enlarged view of a portion of FIG. 21A;

FIG. 22A is a perspective view of an exemplary embodiment of the fixation rod and holding instrument of FIG. 13B as the fixation rod is inserted through a first assembly of FIG. 3A;

FIG. 22B is a perspective view of the assembly of FIG. 3A with the guide sleeve in a first orientation within the assembly;

FIG. 22C is a cross-sectional view of the assembly of FIG. 22B positioned within the body;

FIG. 23A is a perspective view of an exemplary embodiment of the fixation rod and holding instrument of FIG. 13B as the fixation rod is inserted into the body;

FIG. 23B is a perspective view of the assembly of FIG. 3A with the guide sleeve in a second orientation within the assembly;

FIG. 26 is a perspective view of an exemplary embodiment of a spinal fixation system.

DETAILED DESCRIPTION

Figures 3A, 3B:
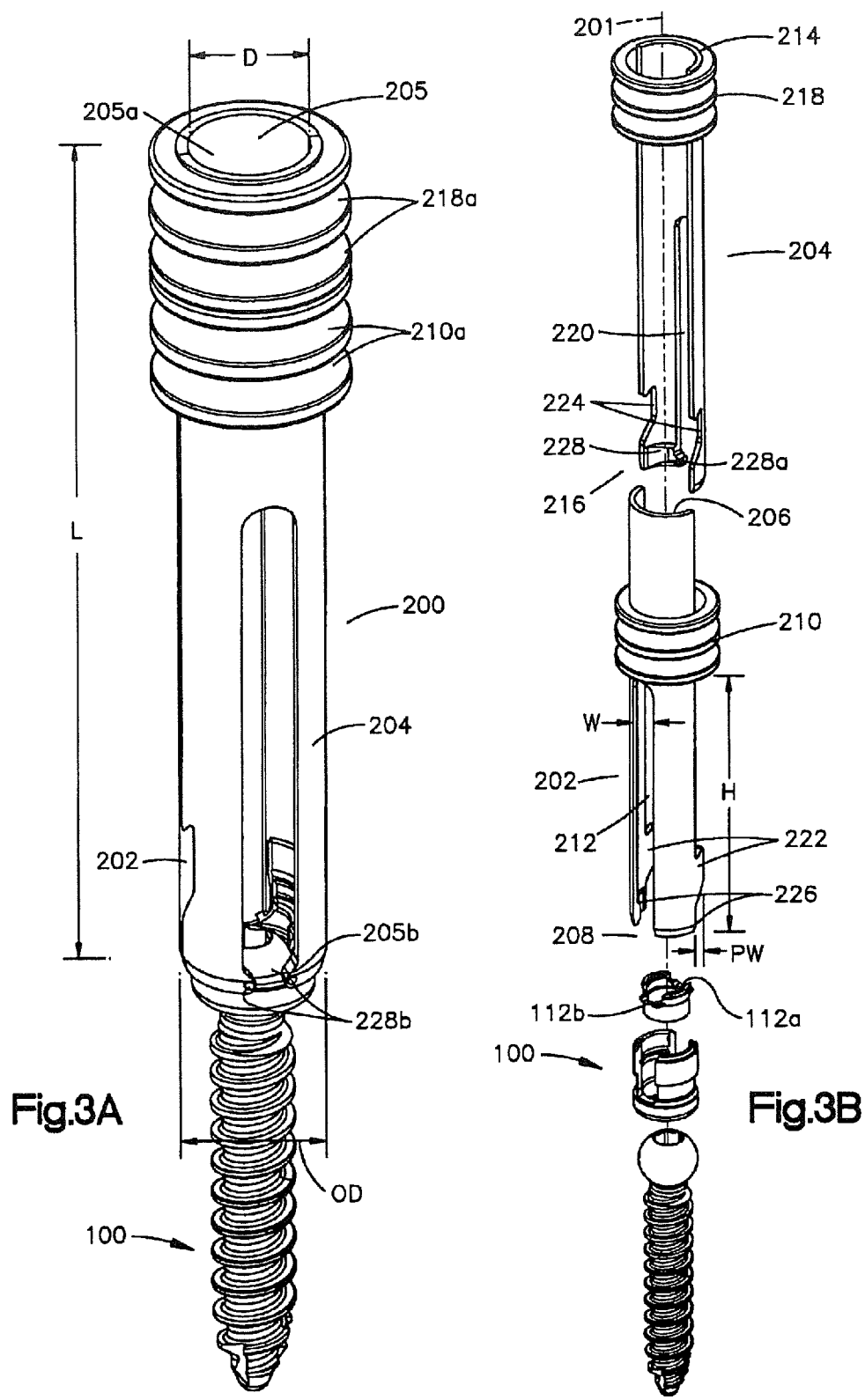
FIG. 3A is a perspective view of an exemplary embodiment of an insertion guide of the present invention attached to the implant of FIG. 1.
FIG. 3B is an exploded view of the insertion guide of FIG. 3A and the implant of FIG. 1.

The method of spinal fixation of the present invention may be performed using various instrumentation, including a plurality of implants (e.g., screws 100), a plurality of insertion guides 200, 300, 350, a sleeve 400, 416, a rod (e.g., a fixation rod 500, 550, 570, 700) and a holding instrument 600, 650, 670, 800. It should, however, be understood that those of ordinary skill in the art will recognize many modifications and substitutions which may be made to various elements of the present invention. Moreover, although the instruments are described herein as being used in connection with spinal fixation procedures, one of ordinary skill in the art will readily appreciate that the instruments may be used in any other parts of the body (e.g., a long bone) to perform a fixation procedure. Thus, the location is not intended to be limiting in any way. In addition, the instruments may be used singularly or in combination with the other instruments described or other instruments that are not described herein. And, while the procedure discussed herein is performed using a posterior approach, those skilled in the art will recognize that the method and instrumentation may be adapted for any type of approach (e.g., posterio-lateral, lateral, anterior, anterio-lateral).

A radiographic image may be taken of the spine, including the vertebrae which are to receive implants such as, for example, pedicle screws and fixation spinal rods. From the radiographic image, one or more insertion points may be located on a patient's back. A surgeon may make an incision in a patient's back to form an opening. The incision may have a length, for example, between about 1 cm and about 10 cm and, more preferably, between about 1.5 cm and about 5 cm. A smaller incision may be used where each insertion guide may be inserted through its own incision and a larger incision may be used where more than one insertion guide may be inserted through a single incision. Preferably the implants are inserted into pedicles of the spine and, thus, the incisions are offset from the central spinous process by, for example, about 15 to about 35 mm. A set of implants may be used on each side of the spinous process.

Thereafter, a guide wire (not shown) may be inserted though the incision and into a vertebrae. A surgical mallet or other impaction instrument (not shown) may be used to strike the guide wire such that the guide wire may be anchored to the vertebra (e.g., into the pedicle of the vertebra). The guide wire may be used to guide various devices and/or implants into a patient and towards the spine. For example, the guide wire may be used to guide dilators, insertion guides, drill bits, screwdrivers, and/or implants (e.g., bone screws) to a location on the spine. It should be noted, however, that any device described herein may be inserted into a patient without the use of the guide wire and/or passageways to the spine maybe formed without the use of the guide wire. It will be appreciated by those skilled in the art that, in some methods, a guide wire may be inserted through an incision after a passageway has been created to the spine.

In one method, the incision may be dilated by, for example, sequential dilation. If a guide wire is first inserted through the incision, dilators may be inserted over the guide wire. If no guide wire is used, one or more dilators may be inserted directly through the skin and tissue. Dilation may be performed, through tissue (e.g., through a muscle), in between tissue segments (e.g., muscle segments) or in between tissue and the spine. It will be understood by those skilled in the art that dilation of an incision may be performed using any number of devices. In another method, a surgeon may insert his/her finger(s) through the incision into the underlying tissue to dilate or dissect muscle and tissue in order to create a cleavage or space through tissue, in between tissue sections (e.g., between the multifidus and the longisimus muscle) or in between tissue and the spine. In this way, the surgeon may create a passageway to the vertebrae and/or palpate anatomical landmarks (e.g., facet joint). The methods described above may be repeated to create additional passageways to the spine. A smaller opening may be used where each insertion guide may be inserted through its own opening and a larger incision(s) may be used where more than one insertion guide may be inserted through the same opening. In an embodiment where each screw and insertion guide is inserted through a single opening, the opening of the passageway may have a diameter, for example, between about 0.5 cm and about 3 cm and, more preferably, between about 1 cm and about 2 cm. It should be noted that the opening may be any shape, for example, oval, circular, egg-shaped, square, rectangular, polygonal or other shapes.

In some methods, an entire procedure may be performed through a single dilated passageway. For example, a procedure may be performed through a cannula or a retractor, which may be expanded after insertion into the body, such as disclosed in U.S. patent application Ser. No. 10/917,560, filed Aug. 13, 2004, entitled Multiple-Blade Retractor, the entire content of which is hereby incorporated by reference. In a method where an entire procedure may be performed through a single incision, after the incision has been fully dilated, a cannula, retractor or insertion guide may be placed into the body either over a dilator or directly into the passageway. In such methods, the opening of the passageway may have a diameter, for example, between about 1.0 cm and about 12 cm and, more preferably, between about 3 cm and about 8 cm.

Once a passageway has been created to the spine, a drill, awl and/or probe may be used to create an opening in one or more vertebrae. An implant (e.g., screw 100 of FIG. 1) may be passed through the passageway and may be inserted into the opening in the vertebrae using a screwdriver. For example, a screw 100 may be inserted into each pedicle of two or more adjacent vertebrae. In other embodiments, the screw 100 may be self threading and/or self tapping so that a tap (if used) may be unnecessary and the screw 100 may be screwed directly into the vertebrae using, for example, a screwdriver.

The screw 100 may comprise a shaft portion 102 and a head portion 104 operably connected to the shaft portion 102. The shaft portion 102 may be threaded. The screw 100 may be polyaxial such that the head portion 104 may articulate and may be rotatable with respect to the shaft portion 102 (e.g., the head 104 may move about more than one axis; a polyaxial screw). Alternatively, the shaft 102 and head portion 104 may be fixed with respect to each other. The shaft 102 may have a bore 106 passing therethrough so that the screw 100 may be positioned over a guide wire. The head portion 104 may have a channel 108 which may be U-shaped and may receive a fixation rod. The head portion 104 may also have inner threads 110 for receiving an end cap 150 (FIG. 26) so that a fixation rod may be held in the channel 108 between the end cap and the surface 112a, 112b of the channel 110. Other end caps and means of holding the spinal rod and/or locking the shaft portion with respect to the head portion may be implemented. Moreover, a groove or recess 114 may be incorporated into the head 104 so that an insertion guide may be attached thereto. It is contemplated, however, that any screw may be used so long as the screw incorporates or may be attached to a rod receiving channel sized and configured to receive a fixation rod. Once the screw 100 is positioned in a vertebrae, the guide wire, if present, may be removed.

While the shaft 102 and head portion 104 may be inserted into the body as a single unit, in other embodiments, the shaft 102 and head portion 104 may be inserted separately. In such an embodiment, the shaft 102 may be inserted into a vertebrae. Thereafter, the head portion 104 may be attached to the shaft. In such an embodiment, the head portion 104 may be attached to an insertion guide 200, 300, 350 and/or other instrument so that the head portion 104 and the insertion guide 200, 300, 350 and/or other instrument may be inserted into the body as a single unit or assembly. The head portion 104 may be attached and/or snapped onto the shaft 102 using the insertion guide 200, 300, 350 and/or other instrument (e.g., a pusher) to provide the surgeon with leverage for exerting force onto the head portion 104.

Furthermore, those skilled in the art will appreciate that the screw 100 may be attached to an insertion guide 200, 300, 350 prior to insertion into the patient's body so that the screw and insertion guide 200, 300, 350 may be inserted into the patient as a single unit. A tool (e.g., screwdriver) may then be inserted through the insertion guide 200, 300, 350 to insert the screw into a vertebrae. Moreover, in another embodiment, an insertion guide 200, 300, 350 may be positioned in the body before the screw 100. One or more tools (e.g., a drill, awl, probe) may be inserted through the insertion guide 200, 300, 350 to create an opening in a vertebrae (e.g., an opening in the pedicle of a vertebrae). A screw 100 may then be inserted down the insertion guide 200, 300, 350, may be attached to the distal end of the insertion guide 200, 300, 350 and inserted into a vertebrae using a screwdriver. In other procedures, a screwdriver (not shown) may also be positioned within the insertion guide 200, 300, 350 and may engage the screw 100 so that the screw 100, insertion guide 200, 300, 350 and screwdriver may be inserted into the body as a single unit. Once the screw 100 has been inserted into a vertebrae, the screwdriver may be removed, leaving the screw 100 and insertion guide 200, 300, 350 positioned in the body. In an embodiment using a guide wire, the screw 100, insertion guide 200, 300, 350 and/or other tool(s) (e.g., drill, screwdriver) may be inserted over the guide wire to the vertebrae.

The type of insertion guide (e.g., insertion guide 200, 300, 350) which may be used in a procedure depends on, for example, the preference of the surgeon, the anatomy of the body and/or the requirements of the surgical procedure. Those skilled in the art will appreciate that any configuration of an insertion guide may be used so long as a fixation rod may be inserted therethrough and the insertion guide may be operably associated with the screw 100 or other implant.

In one embodiment, an insertion guide may be inserted directly through a passageway in a patient without the use of any additional instruments. Thus, the insertion guide may perform the function of dilating/retracting an opening. Furthermore, an insertion guide may be used to move (e.g., rotate) the head portion 104 of the screw 100 so that an operator may align the channels 108 of multiple screws 100 which may be inserted into adjacent vertebrae. In this way, a fixation rod may be inserted into screws 100 positioned in adjacent vertebrae.

The insertion guide 200, 300, 350 may allow a surgeon to directly visualize the orientation of the head portion 104 of the screw 100. As such, a surgeon may be able to verify the location of a fixation rod in the channel 108. To further enhance a surgeon's ability to visualize within the insertion guide 200, 300, 350 and/or into a surgical work site, the insertion guide may have a light source (not shown) integral therewith or attached thereto. In addition, the insertion guide may have a suction-irrigation system (not shown) to remove fluid and/or tissue, which may be obstructing a surgeon's view into the insertion guide 200, 300, 350 and/or may be obstructing a view of a surgical site. A microscope or endoscope (not shown) may also be attached to the insertion guide 200, 300, 350 to provide an enhanced view of a surgical site. Moreover, where a procedure may require stabilization of an insertion guide 200, 300, 350, the insertion guide 200, 300, 350 may be connected to a table mount, which may be attached, for example, to an operating table and may hold the insertion guide 200, 300, 350 in place with respect to the patient, thereby eliminating the need for a surgeon or a nurse to hold the insertion guide 200, 300, 350 during surgery.

The insertion guide 200, 300, 350 and its components may be made, for example, of metal, ceramic, plastic, rubber, a combination of materials or a composite material. For example, the insertion guide 200, 300, 350 and its components may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), or ultra high molecular weight polyethylene (UHMWPE)). The insertion guides 200, 300, 350 may have a non-glare or lubricious coating and/or may be radiolucent or radioopaque. Various factors may be considered when determining the material used to make the insertion guide 200, 300, 350 (or components thereof), including ability to withstand sterilization/cleaning (e.g., using an autoclave; cleaning products used for sterilization in hospitals), weight, durability, ability to withstand forces exerted thereon, resistance to staining (e.g., from blood or substances used in surgery) and the ability to grip the components, particularly with latex gloves which are generally used during surgery. In addition, the components of the insertion guide 200, 300, 350 may be made, for example, by casting, extrusion, injection molding, compression molding, forging, machining, or transfer molding.

As illustrated in FIGS. 3A and 3B, the insertion guide 200 may include a first section or member 202 and a second section or member 204 which may be attachable to each other to form a tube with a bore 205 therethrough. The bore 205 may be sized and configured to receive the head portion 104 of the screw 100 and may have a dimension D of between about 8 mm and about 20 mm, more preferably, between about 9 mm and about 16 mm and, most preferably, between about 10 mm and about 14 mm. The bore 205 may have a proximal opening 205a and a distal opening 205b. It should be noted that the first and second sections 202, 204 may be any shape such that the first and second sections 202, 204 may form a tube which may be, for example, cylindrical, oval, square, rectangular or other polygon (e.g., the sections 202, 204 may be crescent shaped, U-shaped, V-shaped).

The first section 202 may have a proximal end 206, a distal end 208, a first ring member 210 which may be positioned between the proximal end 206 and the distal end 208, and a first longitudinal slot 212. The second section 204 may have a proximal end 214, a distal end 216, a second ring member 218 which may be positioned at the proximal end 214, and a second longitudinal slot 220. The first and second longitudinal slot 212, 220 may extend from the distal end 208 towards the proximal end 206. The first and second longitudinal slots 212, 220 may be sized and configured to receive a fixation rod therethrough. For example, the first and second longitudinal slots 212, 220 may have a width W between about 3 mm and about 7 mm, more preferably, between about 5 mm and about 6.5 mm and, most preferably, between about 5.5 mm and about 6 mm. Moreover, the first and second longitudinal slots 212, 220 may have a height H, for example, between about 10 mm and about 100 mm, more preferably, between about 20 mm and about 80 mm and, most preferably, between about 30 mm and about 60 mm. It should be noted that the first and second longitudinal slots 212, 220 may have the same or different width W and/or height H.

The first and second section 202, 204 may be selectively engageable to each other. For example, the first section 202 may have one or more protrusions 222 which may engage one or more receiving portions 224 of the second section 204. The protrusions 222 and receiving portions 224 may be located anywhere between the proximal ends 206, 214 and distal ends 208, 216. In a preferred embodiment, the protrusions 222 and receiving portions 224 may be located proximate the distal ends 208, 216. The protrusions 222 and receiving portions 224 may be any shape so long as the protrusions 222 and receiving portions 224 may be used to fix the first and second sections 202, 204 with respect to each other. The protrusions 222 and receiving portions 224 may correspond in shape. The protrusions 222 may have a width PW of, for example, between about 1 mm and about 6 mm, more preferably, between about 2 mm and about 5 mm and, most preferably, between about 3 mm and about 4 mm. The receiving portion 224 may have a corresponding width. The protrusions 222 and the receiving portions 224 may be straight (e.g., rectangular) or may be slanted (e.g., a parallelogram) such as shown in FIGS. 3A and 3B. In a preferred embodiment, the protrusions 222 and receiving portions 224 may be slanted allowing for ease of engagement/disengagement of the first and second sections 202, 204 and facilitating engagement/disengagement of the guide 200 with the head portion 104 of the screw 100.

In order to assemble the insertion guide 200, the distal end 216 of the second section 204 may be moved through the first ring member 210 of the first section 202 until the proximal end 206 of the first section 202 may be positioned through the second ring member 218 of the second section 204. In the assembled condition, the rings 210, 218 may be positioned adjacent each other or may be a distance from each other. The rings 210, 218 may be sized and configured so that an operator may use his/her hand and/or fingers to move the sections 202, 204 together or separate the sections 202, 204 by, for example, positioning the ring 218 against a thumb or in the palm of a hand and/or grasping the ring 210 with a finger. The rings 210, 128 may have a textured (e.g., knurled) surface and/or may have grooves 210a, 218a to enhance a surgeon's grip on the sections 202, 204.

When the sections 202, 204 are attached together, the protrusion 222 may engage the receiving portions 224 so that the sections 202, 204 may be fixed with respect to each other. The two-piece construction may permit the distal ends 208, 216 of the first and second sections 202, 204, respectively, to be flexible and, thus, may enable an operator to attach, snap and/or clip the insertion guide 200 (i.e., the distal ends 208, 216 of the sections 202, 204, respectively) to or remove the insertion guide 200 from the head portion 104. When the insertion guide 200 is in the assembled condition, the insertion guide 200 may have a length L of, for example, between about 50 mm and about 300 mm, more preferably, between about 80 mm and about 250 mm and, most preferably, between about 100 mm and about 200 mm, and an outer dimension OD of, for example, between about 5 mm and about 25 mm, more preferably, between about 10 mm and about 20 mm and, most preferably, between about 12 mm and about 18 mm.

In order to hold the insertion guide 200 on the screw 100, the distal ends 208, 216 may have flanges 226, 228, respectively, which may extend into the bore 205 and may be received in the groove 114 of the screw head 104. Such a construction may prevent the insertion guide 200 from being separated from the head portion 104 of the screw 100. Moreover, the flange 228 may have one or more prongs 228a which may extend into the bore 205 and/or the flange 226 may have one or more prongs (not shown) which may also extend into the bore 205. The prongs 228a may be positioned on a portion 228b which may extend into the longitudinal slot 220. Similarly, in an embodiment where the flange 226 has prongs, the prongs may be positioned on a portion which may extend into the longitudinal slot 212. The retaining portions 228a may be positioned against the surfaces 104a, 104b of the head portion 104 and the retaining portions (if present) of the flange 226 may positioned against the identical surfaces 104a, 104b on the other side of the head portion 104. As shown in FIG. 3B, such a configuration may align the U-shaped portions of the channel 108 with the first and second longitudinal slots 212, 220 so that a fixation rod may be moved along the first and second slots 212, 220 and into the channel 108 of the screw 100. Additionally, such a construction may prevent the insertion guide 200 from rotating relative to the head portion 104 and may allow an operator to move (e.g., rotate) the head portion 104 of the screw 100 with the insertion guide 200 during a surgical procedure while the slots 212, 220 and channel 108 remain aligned.

In an alternative embodiment, as shown in FIG. 4, the insertion guide 300 may include a body portion 302 having a bore 304, a proximal end 306, a distal end 308, a proximal opening 300a, a distal opening 300b, a first longitudinal slot 310 and a second longitudinal slot 312. The bore 304 may be sized and configured to receive the head portion 104 of the screw 100 and may have an inner dimension similar to the dimension D of the bore 205 of FIG. 3A. The insertion guide 300 may have a length L2 of, for example, between about 50 mm and about 300 mm, more preferably, between about 80 mm and about 250 mm and, most preferably, between about 100 mm and about 200 mm, and an outer dimension OD2 of, for example, between about 5 mm and about 25 mm, more preferably, between about 10 mm and about 20 mm and, most preferably, between about 12 mm and about 18 mm.

The first and second longitudinal slot 310, 312 may extend from the distal end 308 towards the proximal end 306. The first and second longitudinal slots 310, 312 may be sized and configured to receive a fixation rod therethrough. For example, the first and second longitudinal slots 310, 312 may have a width W2 between about 3 mm and about 7 mm, more preferably, between about 5 mm and about 6.5 mm and, most preferably, between about 5.5 mm and about 6 mm. Moreover, the first and second longitudinal slots 310, 312 may have a height H2, for example, between about 10 mm and about 100 mm, more preferably, between about 20 mm and about 80 mm and, most preferably, between about 30 mm and about 60 mm. It should be noted that the first and second longitudinal slots 310, 312 may have the same or different widths W2 and/or height H2.

Moreover, the insertion guide 300 may have at least one additional slot 314, 316 which may be located between the longitudinal slots 310, 312. The slots 314, 316 may be sized and configured so as to form a plurality of flexible prongs 318. The prongs 318 may flex to enable an operator to engage the insertion guide 300 with (and disengage the insertion guide 300 from) the head portion 104 of a screw 100 (i.e., so that the guide 300 may be clipped onto or removed from the head portion 104). The slots 314, 316 may have a width W3, for example, between about 0.5 mm and about 6 mm, more preferably, between about 1 mm and about 5 mm and, most preferably, between about 2 mm and about 4 mm. Moreover, the slots 314, 316 may have a height H3, for example, between about 10 mm and about 100 mm, more preferably, between about 20 mm and about 80 mm and, most preferably, between about 30 mm and about 60 mm. It should be noted that the slots 314, 316 may have the same or different width W3 and/or height H3.

In order to hold the insertion guide 300 on the screw 100, the distal end 308 of the insertion guide 300 (e.g., the prongs 318) may have flanges 320, which may extend into the bore 304 and may be received in the groove 114 of the screw head 104. Such a construction may prevent the insertion guide 300 from being separated from the head portion 104 of the screw 100. Moreover, the flanges 320 may each have one or more prongs 322a, 322b which may also extend into the bore 304. The prongs 322a, 322b may be positioned on a portion 323a, 323b which may extend into the longitudinal slots 310, 312. The retaining portions 322a may be positioned against the surfaces 104a, 104b and the retaining portions 322b may be positioned against identical surfaces on the opposite side of the head portion 104. Such a configuration may align the U-shaped portions of the channel 108 with the first and second longitudinal slots 310, 312 so that a fixation rod may be moved along the first and second slots 310, 312 and into the channel 108 of the screw 100. Additionally, such a construction may prevent the insertion guide 300 from rotating relative to the head portion 104 and may allow an operator to move the head portion 104 of the screw 100 with the insertion guide 300 during a surgical procedure while the slots 212, 220 and channel 108 remain aligned.

Figure 4A:
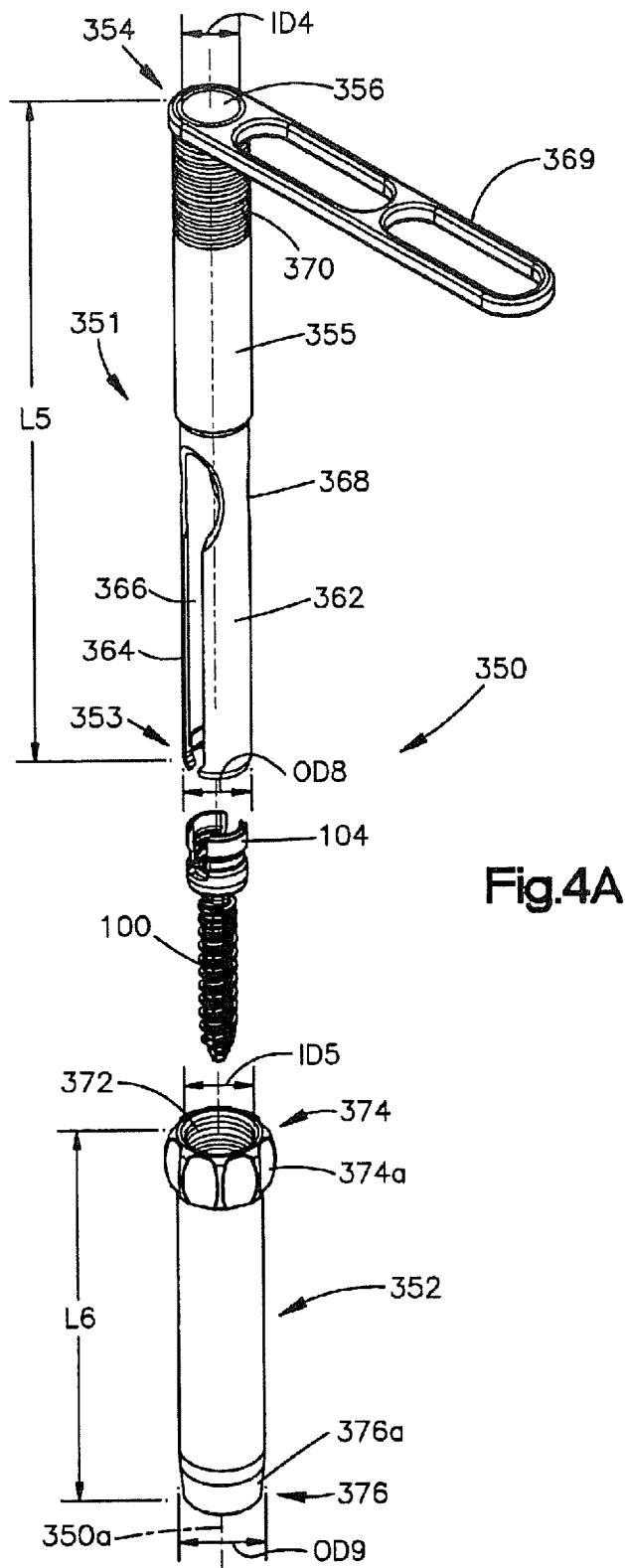
FIG. 4A is an exploded view of another alternative exemplary embodiment of an insertion guide.
Figure 4B:
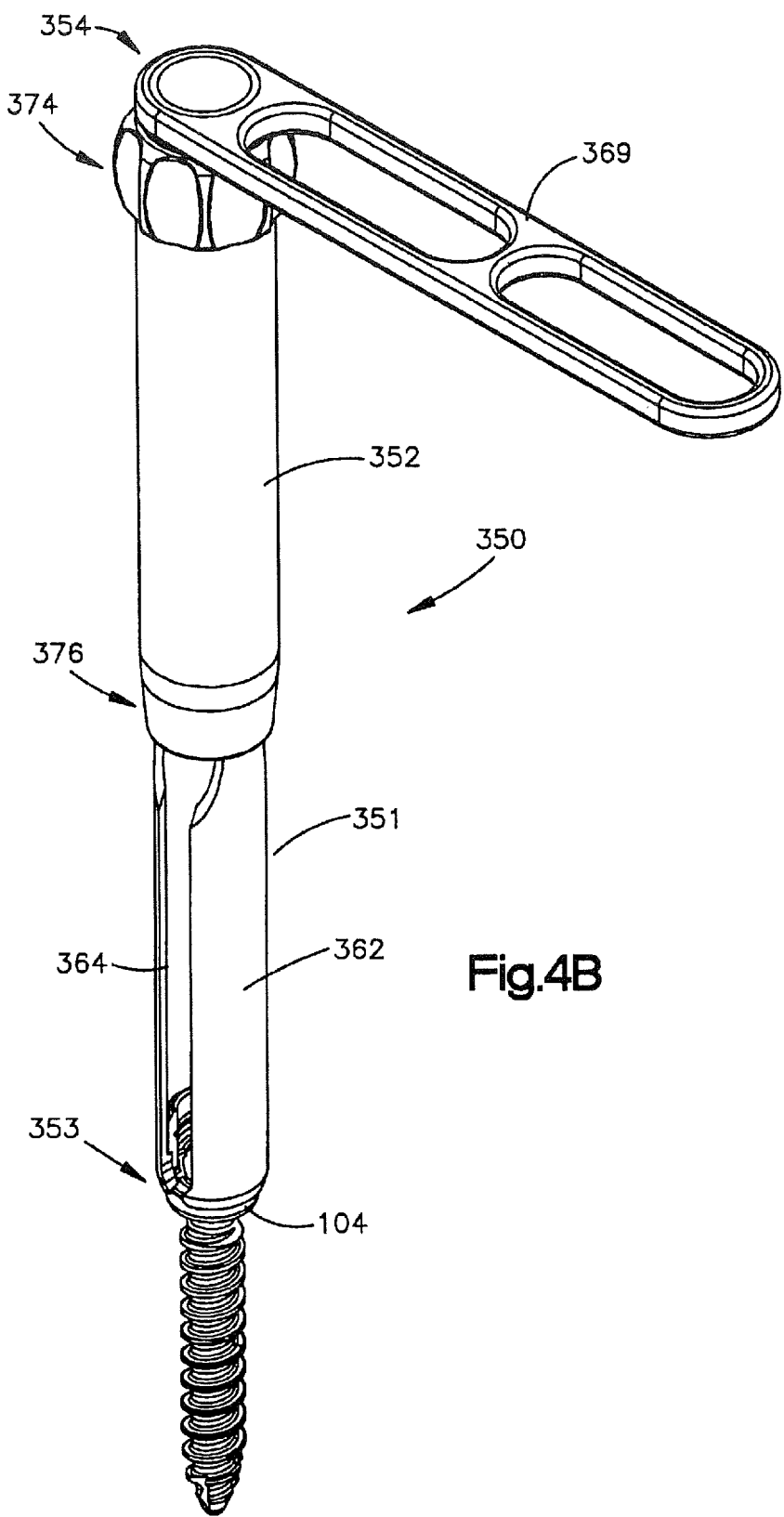
FIG. 4B is a perspective view of the guide of FIG. 4A with an outer sleeve in a first position.
Figure 4C:
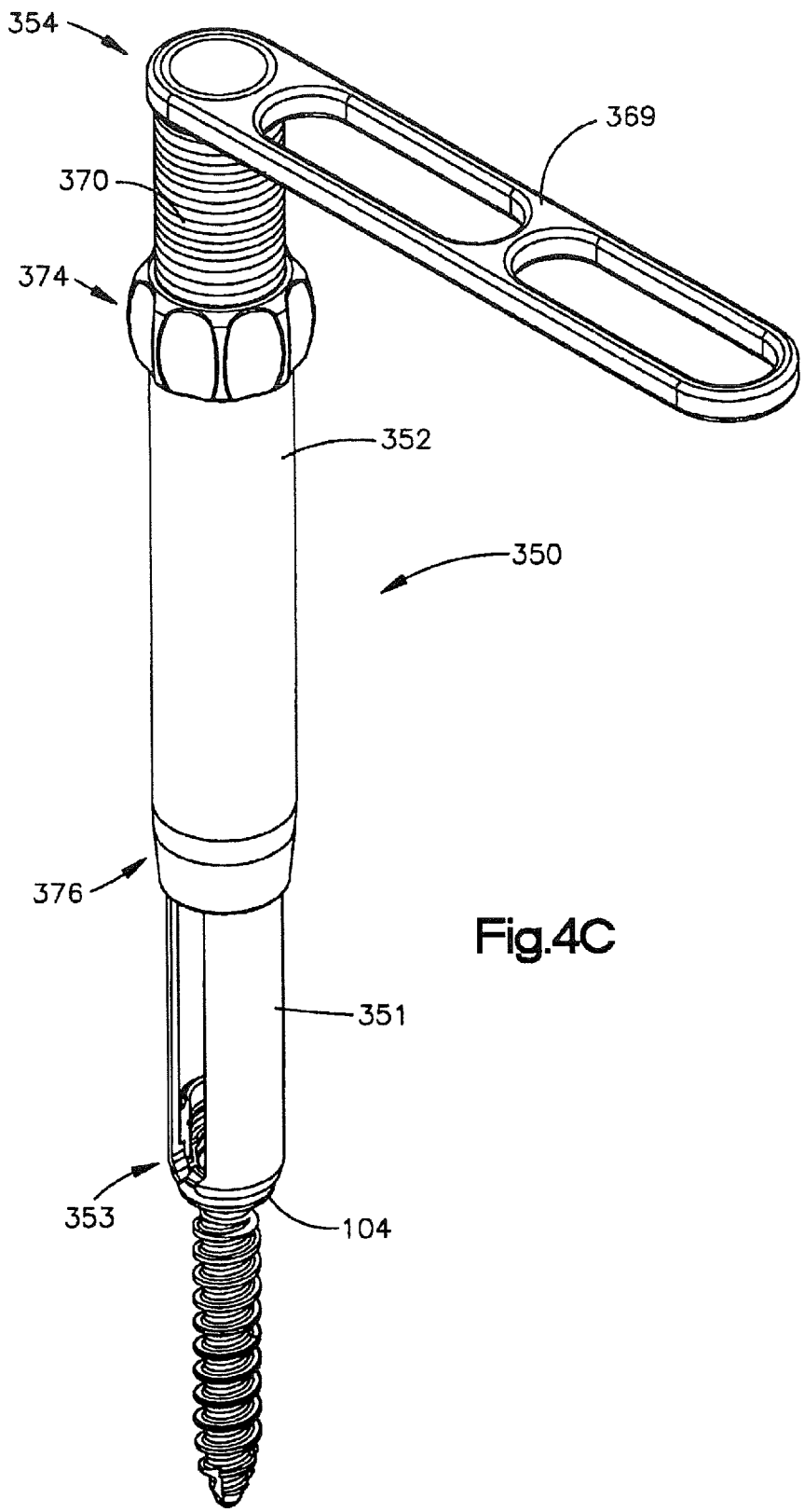
FIG. 4C is a perspective view of the guide of FIG. 4A with an outer sleeve in a second position.

FIG. 4A illustrates an alternative embodiment of an insertion guide 350. The insertion guide 350 may have an inner sleeve 351 and an outer sleeve 352. The inners sleeve 351 may have a distal end 353, a proximal end 354, and a bore 356 passing from the distal end 353 to the proximal end 354. The bore 356 may be sized and configured to receive the head portion 104 of the screw 100 and may have an inner dimension ID4 of, for example, between about 8 mm and about 20 mm, more preferably, between about 9 mm and about 16 mm and, most preferably, between about 10 mm and about 14 mm. The inner sleeve 351 may have a length L5 of, for example, between about 50 mm and about 300 mm, more preferably, between about 80 mm and about 250 mm and, most preferably, between about 100 mm and about 200 mm, and an outer dimension OD8 of, for example, between about 5 mm and about 25 mm, more preferably, between about 10 mm and about 20 mm and, most preferably, between about 12 mm and about 18 mm.

The inner sleeve 351 may have body portion 355, and first and second arms 362, 364 extending from the body portion 355. The arms 362, 364 may have a first longitudinal slot 366 and a second longitudinal slot 368 therebetween such that the arms 362, 364 may be flexible relative to each other. An integral or detachable handle 369 may be attached to the inner sleeve 351 (e.g., proximate the proximal end 354) and may be used by a surgeon to manipulate the insertion guide 350 during a surgical procedure. In addition, the inner sleeve 351 may have an actuating mechanism (e.g., threads 370, a ratchet mechanism), which may extend along a portion of the inner sleeve 358. For example, in an embodiment with threads 370, the threads 370 may extend along the body 355 from the proximal end 354 towards the distal end 353.

The outer sleeve 352 may be positioned over the inner sleeve 351 and may have an inner dimension ID5 which may be sized to fit over the inner sleeve 351. The outer sleeve may have a length L6 of, for example, between about 30 mm and about 200 mm, more preferably, between about 50 mm and about 160 mm and, most preferably, between about 75 mm and about 125 mm and an outer dimension OD9 of, for example, between about 6 mm and about 30 mm, more preferably, between about 10 mm and about 25 mm and, most preferably, between about 12 mm and about 20 mm. The outer sleeve 352 may also have an engagement member (e.g., internal threads 372) which may engage the threads 370 of the inner sleeve 351. An operator may move the outer sleeve 352 along the inner sleeve 351, for example, by rotating the outer sleeve 352 about the inner sleeve 351 (i.e., about axis 350a). A knob 374a may be provided to enhance a surgeon's grip of the outer sleeve 352 to facilitate rotation. The outer sleeve 352 may have a first position on the inner sleeve 351 (FIG. 4B), where the proximal end 374 of the outer sleeve 352 may be positioned proximate the proximal end 354 of the inner member 351 (i.e., the proximal end 374 may be a first distance from the proximal end 354), and a second position (FIG. 4C), where the proximal end 374 of the outer sleeve 352 is moved farther away from the proximal end 354 of the inner member 351 (i.e., the proximal end 374 may be a second distance from the proximal end 354 and the second distance may be greater than the first distance).

When the outer sleeve 352 is in a first position, the head portion 104 of a screw 100 may be inserted in between arms 362, 364. In order to hold the insertion guide 350 on the screw 100, the distal ends 362a, 364a of the arms 362, 364, respectively, may have flanges 376, which may extend into the bore 356 and may be received in the groove 114 of the screw head 104. It should be noted that only one arm may have a flange 376. The flange(s) 376 may prevent the insertion guide 350 from being separated from the head portion 104 of the screw 100. In some embodiments, the flange 376 may extend along the entire distal ends 362a, 364a of the arms 362, 364, respectively, or may be positioned only on a portion of the arms 362, 364. Moreover, each flange 376 may have one or more extending portions 378 which may extend into the longitudinal slots 366 and/or 368 and which may be positioned in a retaining portion 380 of the head portion 104 proximate the channel 108. Such a configuration may prevent the insertion guide 350 from rotating relative to the head portion 104 of the screw 100. Those skilled in the art will appreciate that any configuration which prevents the guide 350 from rotating relative to the screw 100 may be used. Once the inner sleeve 351 is positioned on the screw 100, the outer sleeve 352 may be moved from the first position (FIG. 4B) to the second position (FIG. 4C), thereby firmly engaging the arms 362, 364 around the head portion 104. The outer sleeve 352 may have a tapered end 376a to facilitate introduction of the outer sleeve 352 and/or the insertion guide 350 into the body.

Figure 4E:
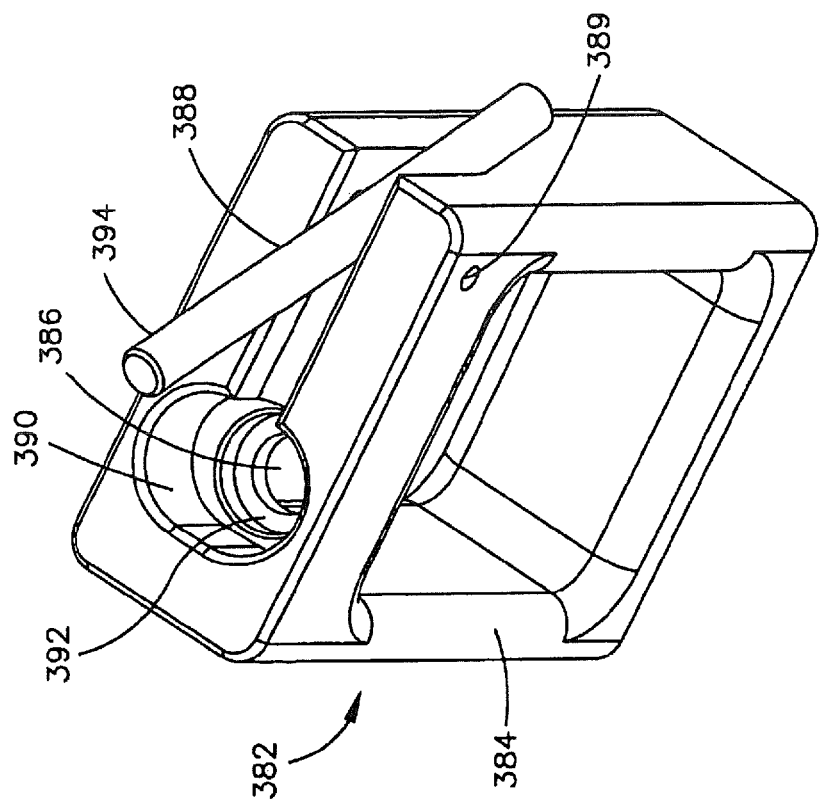
FIG. 4E is a perspective view of an exemplary embodiment of a holder.
Figure 4D:
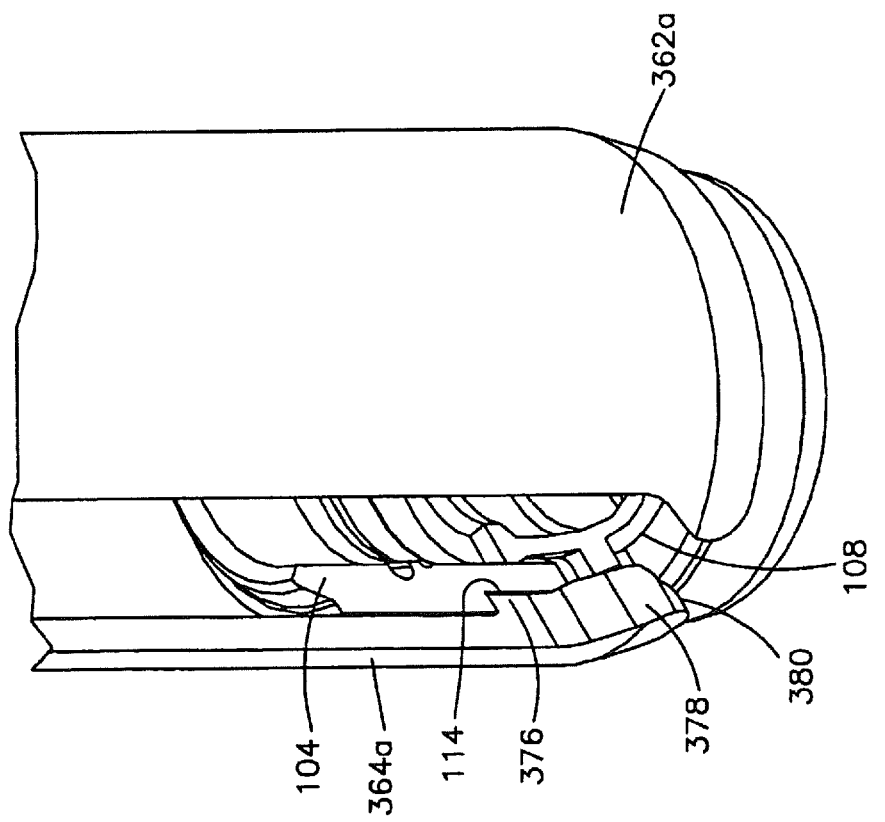
FIG. 4D is a perspective view of an end of the insertion guide of FIG. 4C.
Figure 11A:
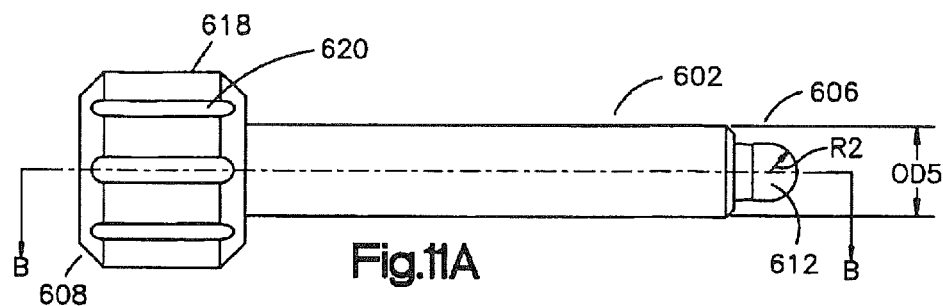
FIG. 11A is a side view of an exemplary embodiment of an outer member of the holding instrument of FIG. 9.
Figure 11B:
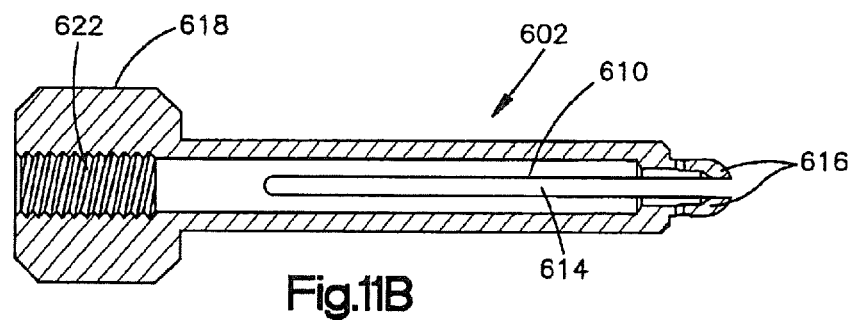
FIG. 11B is a cross-sectional view of the outer member of FIG. 11A along B-B.

As shown in FIGS. 4E and 4F, a holder 382 may be used by a surgeon to connect a screw 100 and insertion guide 350. The holder 382 may have a body 384, an opening 386 for receiving the screw 100, and a fixing member 388 for holding the screw 100 in a fixed position relative to the holder 382 (i.e., so that the head portion 104 of the screw 100 may be prevented from rotating relative to the holder 382). In one embodiment, the fixation member 388 may be a rod and may be rotatably connected to the holder 382 about a pivot 389. The components of the holder 382 may be made, for example, of metal, ceramic, plastic, rubber, a combination of materials or a composite material. For example, the components may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), or ultra high molecular weight polyethylene (UHMWPE)). Various factors may be considered when determining the material used to make the components, including ability to withstand sterilization/cleaning (e.g., using an autoclave; cleaning products used for sterilization in hospitals), weight, durability, ability to withstand forces exerted thereon, resistance to staining (e.g., from blood or substances used in surgery) and the ability to grip the components, particularly with latex gloves which are generally used during surgery.

The holder 382 may also have a counterbore 390 which may be positioned adjacent the opening 386 and may receive the distal end 353 of the inner sleeve 351. The counterbore 390 may be non-circular so that the insertion guide 350 may be prevented from rotating within the counterbore 390 when inserted therein. Moreover, in order to prevent the holder 382 from tipping/falling over during insertion of an insertion guide 350, the holder 382 may also be configured to be operably attached to another object (e.g., operating table or tool kit) by a fastener (e.g., bolt, screw, Velcro). In some embodiments, the holder 382 may be made of a heavy material so that the holder 382 is weighed down.

In use, a screw 100 may be inserted through the opening 386 so that the head portion 104 of the screw 100 may rest against a ledge 392 and the shaft 102 may be positioned through the hole 386. Thereafter, as shown in FIG. 4F, the retaining member 388 may be rotated so that an end portion 394 of the retaining member 388 may be positioned within the channel 108 of the head portion 104, thus, fixing the screw 100 with respect to the holder 382. An insertion guide 350 may then be connected to the head portion 104. In particular, the arms 362, 364 of the inner sleeve 351 may be positioned around the head portion 104 so that the retaining member 388 may be positioned through one or both longitudinal slots 366, 368. The outer sleeve 352 may then be rotated so that the distal end 376 of the outer sleeve 352 moves towards the distal end 353 of the inner sleeve 351 until the arms 362, 364 firmly engage the head portion 104. The screw 100 and insertion guide 350 may subsequently be removed from the holder 382 and inserted into the body as a single unit. This step may be repeated for additional insertion guides 350. It should be noted, however, that a holder 382 may be unnecessary and a surgeon may attach the screw 100 and insertion guide 350 using only his/her hands/fingers.

FIG. 5 illustrates a screw 100 positioned in the pedicle of a first vertebrae V1 with an insertion guide (e.g., insertion guide 200a) attached thereto and extending out of a first incision I1 in the skin. It should be noted that FIG. 5 is for illustrative purposes only and any insertion guide (e.g., guide 300) may be attached to a screw 100 at any vertebral body. The method of inserting screw 100 and insertion guide 200, 300, 350 may be repeated one or more times. For example, as shown in FIGS. 6 and 7, a screw 100 may be inserted in a second and third vertebrae V2, V3 (e.g., in the pedicle) with insertion guides (e.g., insertion guides 200b, 200c) attached thereto and extending out of a second and third incision 12, 13, respectively, in the skin. Such a construction may allow for spinal fixation of the three vertebrae V1, V2 and V3. While FIGS. 5, 6 and 7 illustrate a procedure being performed through three separate incision I1, I2 and I3, it should be noted that the three screws 100 and insertion guides may be positioned in the same incision, cannula and/or retractor such that a spinal fixation procedure may be performed through one larger incision.

Once the screws 100 and insertions guide have been inserted into the body, a guide sleeve 400, 416 may be positioned through at least one insertion guide. For example, the guide sleeve 400 may be inserted into insertion guide 200a, 200b or 200c. Generally, the guide sleeve 400, 416 would be inserted in one of the end insertion guides 200a or 200c. The guide sleeve 400, 416 may be sized and configured to fit within the bore 205, 304, 356 of the insertion guide 200, 300, 350. The sleeve 400 may have an outer dimension OD3 of, for example, between about 5 mm and about 22 mm, more preferably, between about 10 mm and about 18 mm and, most preferably, between about 12 mm and about 16 mm, and an inner dimension ID3 of, for example, between about 4 mm and about 21 mm, more preferably, between about 9 mm and about 17 mm and, most preferably, between about 10 mm and about 15 mm. The sleeve 400 may also have a length L3 of, for example, between about 50 mm and about 350 mm, more preferably, between about 80 mm and about 270 mm and, most preferably, between about 100 mm and about 210 mm. Alternatively, the guide sleeve 400, 416 may be sized and configured to fit over the outside of the insertion guide 200a, 200b or 200c. For example, a guide sleeve 400, 416 may be positioned over the distal end 208, 216 of the insertion guide 200 (or over the distal end 308 of insertion guide 300 or distal end 353 of inner sleeve 351) prior to insertion of the insertion guide 200, 300, 350 into the body. Thereafter, the insertion guide 200, 300, 350 and sleeve 400, 416 may be inserted into the body as a single unit. The sleeve 400, 416 may be rotated about insertion guide 200, 300, 350 for reasons which will become apparent below. In another embodiment, the sleeve 400, 416 may be made of two pieces which may be inserted over the outside of an insertion guide 200, 300, 350 and connected to each other. Alternatively, the sleeve 400, 416 may be made of two pieces connected by a hinge so that the sleeve 400, 416 may be opened to fit around the insertion guide 200, 300, 350 and closed therearound. It will be appreciated by those skilled in the art that, in some embodiments, the sleeve 400, 416 may be inserted over the proximal end of an insertion guide (i.e., the portion of the insertion guide positioned outside the body) before or after the insertion guide is inserted into the body. For example, the sleeve 400, 416 may be inserted over the proximal end 306 of the insertion guide 300.

As shown in FIGS. 8A and 8B the guide sleeve 400 may include a body 402 which may have a longitudinal axis 401, a proximal end 404, a proximal opening 400a, a distal end 406, a distal opening 400b and a bore 407 extending from the proximal end 404 to the distal end 406. The length L3 of the sleeve 400 may be long enough such that the proximal end 404 of the sleeve 400 may protrude from the proximal end 214, 306, 354 of the insertion guides 200, 300, 350, respectively. Such a construction may allow a surgeon to manipulate the sleeve 400 during surgery as described in greater detail below. Moreover, the distal end 406 of the guide sleeve 400 may have a chamfered inner edge 406c which may engage a corresponding chamfered edge 104c of the head portion 104 of the screw 100. The chamfered edges 104c and 406c may be sloped in opposite directions so that the chamfered edges 104c and 406c may be positioned adjacent each other.

The body 402 may also have a first opening 408, a second opening 410, a first longitudinal opening 412 intersecting the first opening 408 and a second longitudinal opening 414 intersecting the second opening 410. For example, the first and second openings 408, 410 may be at an angle (e.g., perpendicular) with respect to the first and second longitudinal opening 412, 414, respectively. The first and second openings 408, 410 preferably are formed in a side wall 400s of the generally cylindrical sleeve body 402 and are elongated preferably perpendicular to the longitudinal axis 401 of the sleeve body 402. The first and second longitudinal openings 412, 414 preferably are formed in the side wall 400s of the sleeve body 402 and extend in the direction of the longitudinal axis 401 of the sleeve body 402. The first longitudinal opening 412 and second longitudinal opening 414 may extend from the distal end 406 towards the proximal end 404. Preferably, the first opening 408 is generally perpendicular to the first longitudinal opening 412 to form a generally L-shaped opening in the side wall 400s of the sleeve body 402. Preferably the second opening 410 is generally perpendicular to the second longitudinal opening 414 to form a generally L-shaped opening the side wall 400s of the sleeve body 402. Preferably, the first longitudinal opening 412 is opposite (formed about 180° from) the second longitudinal opening 414. Although the first and second openings 408, 410 have been shown and described as being generally perpendicular to the first and second longitudinal openings 412, 414, respectively, the first and second openings 408, 410 may be formed at an angle from about 0° to about 180° with respect to the first and second longitudinal openings 412, 414, respectively, and may form different shapes other than a generally L-shaped opening. The first and second openings 408, 410 and first and second longitudinal openings 412, 414 may be sized and configured to receive a fixation rod, more preferably, the width of the first and second opening 408, 410, as well as the width of the first and second longitudinal openings 412, 414 may be slightly larger than the diameter of a spinal rod so that a spinal rod can be passed through the respective openings.

The first longitudinal opening 412 may have a height H3 of, for example, between about 10 mm and about 100 mm, more preferably, between about 20 mm and about 80 mm and, most preferably, between about 30 mm and about 60 mm. The second longitudinal opening 414 may have a height H4 of, for example, between about 8 mm and about 100 mm, more preferably, between about 15 mm and about 70 mm and, most preferably, between about 20 mm and about 60 mm. The first and second longitudinal openings 412, 414 may have a width W3 of, for example, between about 3 mm and about 7 mm, more preferably, between about 5 mm and about 6.5 mm and, most preferably, between about 5.5 mm and about 6 mm. The first and second longitudinal openings 412, 414 may have the same or different width W3. Moreover, the first and second openings 408, 410 may have a width W4 of, for example, between about 5 mm and about 30 mm, more preferably, between about 6 mm and about 20 mm and, most preferably, between about 8 mm and about 14 mm. The first and second openings 408, 410 may have the same or different width W4. The width W3 of the first and second longitudinal openings 412, 414 may be the same as or different from the width W4 of the first and second openings 408, 410.

The guide sleeve 400 may be made, for example, of metal, ceramic, plastic, rubber, a combination of materials or a composite material. For example, the sleeve 400 may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), or ultra high molecular weight polyethylene (UHMWPE)). The sleeve 400 may have a non-glare or lubricious coating and/or may be radiolucent or radioopaque. Various factors may be considered when determining the material used to make the sleeve 400, including ability to withstand sterilization/cleaning (e.g., using an autoclave; cleaning products used for sterilization in hospitals), weight, durability, ability to withstand forces exerted thereon, resistance to staining (e.g., from blood or substances used in surgery) and the ability to grip the components, particularly with latex gloves which are generally used during surgery. In addition, the sleeve 400 may be made, for example, by casting, extrusion, injection molding, compression molding, forging, machining, or transfer molding.

FIG. 8C illustrates an alternative embodiment of the sleeve, sleeve 416. The sleeve 416 may have a side wall 418, a proximal end 418a, a distal end 418b, and a bore 419 therethrough extending from the proximal end 418a to the distal end 418b. The sleeve 416 may have the same dimensions and may be made of the same material(s) as the sleeve 400. In addition, the sleeve 416 may have two spiral slots 420, 422. Slot 420 may have a height H5 which may be similar to the height H3 and slot 422 may have a height 116 which may be similar to the height H4. Moreover, the slots 420, 422 may have the same width as the slots 412, 414. Similar to sleeve 400, the sleeve 416 may be positioned through an insertion guide 200a, 200b, 200c, preferably an end insertion guide 200a or 200c. In one embodiment, a rod 500, 550, 570, 700 may be positioned into the insertion guide 200c, through the proximal ends 420a, 422a of the slots 420, 422 and into additional insertion guides 200a, 200b. Thereafter, the sleeve 416 may be rotated so that the rod 500, 550, 570, 700 may be moved down the sleeve 416 towards the distal end 418b of the sleeve 416. The rod 500, 550, 570, 700 may be pushed down into the body (i.e., towards the screws 100) using a holding instrument 600, 650, 670, 800 at the same time the sleeve 416 is being rotated. In this way, tissue may be moved by the rod 500, 550, 570, 700. It should be noted, however, that rotation of the sleeve 416, by itself, may provide sufficient force on the rod 500, 550, 570, 700 so that the rod 500, 550, 570, 700 pushes tissue out of the way as the rod 500, 550, 570, 700 moves down towards the screws 100.

A holding instrument may be used to insert a fixation or spinal rod through the guide sleeve 400, 416 and insertion guides 200, 300, 350 and into the head portion 104 of a screw 100. FIG. 9 illustrates one embodiment of a spinal rod 500 and a holding instrument 600. The rod 500 and/or holding instrument 600 may be made, for example, of metal, ceramic, plastic, rubber, a composite material, or a combination of materials. For example, the rod 500 and/or holding instrument 600 (or components thereof) may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), or ultra high molecular weight polyethylene (UHMWPE)). Various factors may be considered when determining the material used to make the rod 500 and/or holding instrument 600 (or components thereof), including ability to withstand sterilization/cleaning (e.g., using an autoclave; cleaning products used for sterilization in hospitals), weight, durability, ability to withstand forces exerted thereon, resistance to staining (e.g., from blood or substances used in surgery) and the ability to grip the components, particularly with latex gloves which are generally used during surgery. In addition, various methods may be used to make the rod 500 and/or holding instrument 600 (or components thereof), including casting, extrusion, injection molding, compression molding, forging, machining, or transfer molding. These same materials and methods may be used to make any rod and/or holding instruments (or components thereof) such as, for example, rod 700 and holding instrument 800 discussed in greater detail below.

As shown in FIG. 10A, the rod 500 may be a curved elongated member and may be made of a solid piece of material. Alternatively, the rod may be a straight elongated member and/or may be hollow. The rod 500 may have a proximal end 502, a distal end 504, and a cross-section which may be any shape (e.g., round, oval, square, rectangular or other polygon). The rod 500 may be sized and configured to be inserted through the openings/slots in insertion guides 200, 300, 350, guide sleeve 400, 416 and into the channel 108 in the head portion 104 of a screw 100. The rod 500 may have an outer diameter OD4, for example, between about 3 mm and about 7 mm, more preferably, between about 5 mm and about 6.5 mm and, most preferably, between about 5.5 mm and about 6 mm. The length L4 of the rod 500 may be, for example, between about 30 mm and about 200 mm, more preferably, between about 35 mm and about 180 mm and, most preferably, between about 40 mm and about 150 mm, and the length L4 of the rod 500 may be a factor of, for example, the number of screws 100 through which the rod 500 will be inserted and/or the distance in between screws 100 (which may be dictated by patient anatomy). In an embodiment where the rod 500 is curved, the radius of the curvature R1 may be, for example, between about 50 mm and about 500 mm, more preferably, between about 80 mm and about 300 mm and, most preferably, between about 100 mm and about 200 mm.

The distal end 504 of the rod 500 may be round, blunted have a point and/or taper, which may help facilitate moving tissue around the distal end 504 as the rod 500 is inserted through the body. The distal end 504 may have a radius of curvature R of, for example, between about 2 mm and about 15 mm, more preferably, between about 3 mm and about 12 mm and, most preferably, between about 5 mm and about 10 mm. As shown in FIGS. 10A and 10B, the proximal end 502 may have a receiving portion 506 for attaching to at least a portion (e.g., attachment portion 612) of the holding instrument 600. As illustrated in FIG. 9, in one embodiment, the receiving portion 506 may have a side wall 512 that forms a generally U-shaped configuration. The receiving portion 506 may be sized and configured to engage the holding instrument 600 such that the rod 500 may rotate and/or pivot about 360 degrees relative to the holding instrument 600 about an axis 508 and/or may rotate and/or pivot about 100 degrees relative to the holding instrument 600 about an axis 510. The side wall 512 of the receiving portion 506 may have at least one bore 514, which may extend entirely through the wall 512 or partially into the wall 512 (e.g., forming a recess or aperture). The bores 514 may receive corresponding portions (e.g., hemispherical portions 616) of the holding instrument 600. In an embodiment with a recess, the recess may be hemispherical in shape and may receive hemispherical portions 616 of the holding instrument 600.

As shown in FIGS. 11A, 11B, 12A and 12B, the holding instrument 600 may comprise an outer member 602 and an inner member 604. The outer member 602 may have a distal end 606, a proximal end 608 and a passageway 610 which may extend from the distal end 606 to the proximal end 608. The outer member 602 may have an outer dimension OD5 which may be sized and configured to be similar or identical to the outer dimension OD4 of the rod 500. The distal end 606 may have an attachment portion 612 which may be nearly spherical or hemispherical in shape. The attachment portion 612 may be sized and configured to be inserted into the receiving portion 506 of the rod 500. For example, the attachment portion 612 may have a radius of curvature R2 of, for example, between about 1 mm and about 6 mm, more preferably, between about 1.5 mm and about 4 mm and, most preferably, between about 2 mm and about 3 mm.

A slit 614 may pass through the attachment portion 612 and may extend from the distal end 606 towards the proximal end 608. The slit 614 may result in the attachment portion 612 having two spherical like or quadrant portions 616. Such a construction may enable the attachment portion 612 to be flexible so that the attachment portion 612 may be inserted into the receiving portion 506 of the rod 500 and, in particular, so that the hemispherical portions 616 may be inserted and/or snapped into the bores (recesses/apertures) 514 of the rod 500.

The proximal end 608 of the holding instrument 600 may have a enlarged portion 618 which may provide a gripping surface for an operator to manipulate the outer member 602, the holding instrument 600 and/or the rod 500. The enlarged portion 618 may have one or more grooves 620 to provided an enhanced gripping surface for an operator. In one embodiment, the enlarged portion 618 may be textured (e.g., knurled) to provide an enhanced gripping surface. The passageway 610 may have a engagement portion 622, which may be at the proximal end 608. The engagement portion 622 may be a threaded portion and may be used to engage a corresponding engagement portion 624 (such as, for example, threads) of the inner member 604.

Figure 12A:
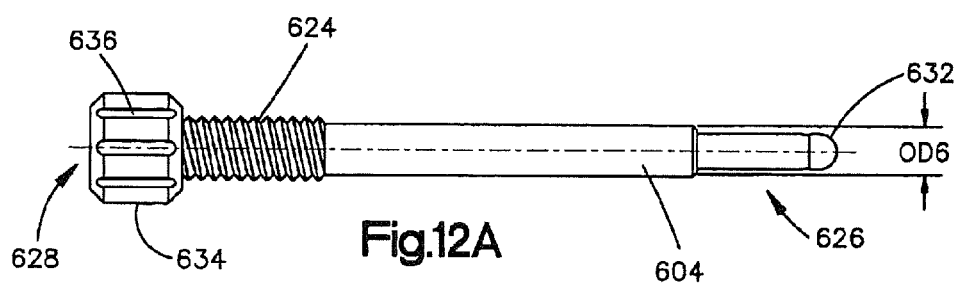
FIG. 12A is a side view of an exemplary embodiment of an inner member of the holding instrument of FIG. 9.
Figure 12B:
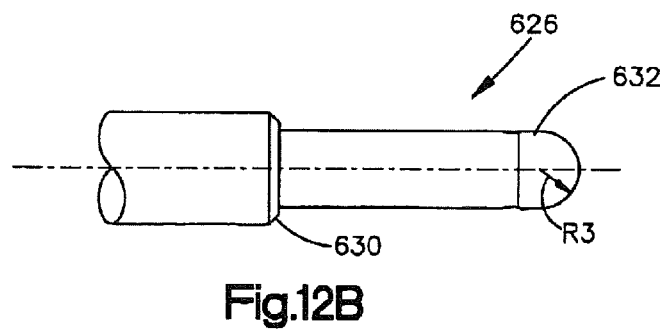
FIG. 12B is an enlarged view of an end of the inner element of FIG. 12A.

As shown in FIGS. 12A and 12B, the inner member 604 may comprise a distal end 626, a proximal end 628, and an engagement portion 624 between the distal end 626 and proximal end 628. The inner member 604 may have an outer dimension OD5 which may be sized and configured such that the inner member 604 may be receiving in the passageway 610 of the outer member 602 and may be moveable therein, both rotationally and by axial sliding. The outer dimensions OD6 may be, for example, between about 2 mm and about 5 mm, more preferably, between about 2.5 mm and about 4.5 mm and, most preferably, between about 3 mm and about 4 mm.

The distal end 626 have a reduced dimension as compared with the outer dimension OD6 of the inner member 604. One way to accomplish this may be to provide a bevel 630 along the length of the inner member 604 and reduce the dimension of the inner rod 604 in the distal direction after the bevel 630. A tip 632 may be formed at the distal end 626 and may be round, blunted, tapered, pointed or any other shape. For example, the tip 632 may have a radius of curvature R3 of between about 0.3 mm and about 1.5 mm, more preferably, between about 0.5 mm and about 1.3 mm and, most preferably, between about 0.7 mm and about 1 mm. The proximal end 628 of the inner member 604 may have an enlarged portion 634 which may provide a gripping surface for an operator to manipulate the inner member 604, the outer member 602, the holding instrument 600 and/or the rod 500. The enlarged portion 634 may have one or more grooves 636 to provided an enhanced gripping surface for an operator. In one embodiment, the enlarged portion 634 may be textured (e.g., knurled) to provide an enhanced gripping surface.

In use, the attachment portion 612 of the outer member 604 may be positioned in the receiving portion 506 of the rod 500. The inner member 604 may be positioned within the passageway 614 of the outer member 602 and moved so that the engagement portion 624 of the inner member 604 may engage the engagement member 622 of the outer member 602. Rotation of the inner member 604 in a first direction (e.g., clockwise) may move the distal portion 626 of the inner member 604 in between the hemispherical portions 616. As the inner member 604 is rotated in the first direction and the distal portion 626 of the inner member 604 is moved in between the hemispherical portions 616, the distal portion 626 may push the hemispherical portion 616 outward, into the bores 514 of the receiving portion 506. Such a configuration may prevent the rod 500 and the holding instrument 600 from separating from each other while, at the same time, may allow for the rod 500 and holding instrument 600 to rotate and pivot relative to each other. In order to fix the angular orientation of the rod 500 and the holding instrument 600 with respect to each other, the inner member 604 may be threaded farther into the outer member so that the tip 632 of the inner member 604 may extend beyond the distal most portion 606 of the outer member 602. The tip 632 may then be inserted into the recess 506a or 506b of the receiving portion. When the tip 632 is positioned in the recess 506b, the holding instrument 600 may be held at an angle with respect to the rod 500 such as shown in FIG. 9. When the tip 632 is positioned in the recess 506a, the axis 500a of the rod 500 may be aligned with the axis 600a of the holding instrument 600 such as shown in FIG. 21A. The rod 500 and holding instrument 600 may be separated from each other by rotating the inner member 604 in a second direction (e.g., counterclockwise) so that the distal end 626 of the inner member 604 may be moved away from the distal end 606 of the outer member 602. With the distal end 626 of the inner member 604 removed from in between the portions 616, the attachment portion 612 of the outer member 602 may be flexed and may be removed from the receiving portion 506 of the rod 500.

FIG. 9A illustrates an alternative rod 550 and holding instrument 650. The rod 550 may have a engaging portion 552 which may be engaged by the holding instrument 650. The holding instrument 650 may have an inner sleeve 651 and an outer sleeve 652. The inner sleeve 651 may have a plurality of arms 654 (e.g., three arms) which may engage the engaging portion 552. The engaging portion 552 may be spherical in shape and the arms 654 may be positioned around the engaging portion 552. The arms 654 may have curved surfaces 656 which correspond to the shape of the engaging portion 552. The outer sleeve 652 may have a first position, where the distal end 652a of the outer sleeve 652 may be positioned away from the arms 654, and a second position (shown in FIG. 9A), where the distal end 652a of the outer sleeve 652 may be positioned proximate (e.g., over) the arms 654. In use, the arms 654 may be attached to the engaging portion 552 when the outer sleeve 652 is in the first position. The arms 654 may be clipped/snapped onto the engaging portion 552. In this configuration, the rod 550 may be pivotable relative to the holding instrument 650 about more than one axis. In order to fix the orientation of the rod 550 with respect to the holding instrument 650, the outer sleeve 652 may be moved from the first position to the second position. With the distal end 652a of the outer sleeve 652 positioned over the arms 654, the arms 654 may be firmly held against the engaging portion 552, thereby fixing the position of the rod 550 relative to the holding instrument 650.

FIG. 9B shows another embodiment of a rod 570 and holding instrument 670. The rod 570 may have an engagement portion 572 which may be any shape (e.g., circular, polygonal) and may have one or more flat surfaces 574. The holding instrument 670 may have an inner sleeve 672 and an outer sleeve 674. The inner sleeve 672 may have a pair of prongs 676 which may be sized and configured to be positioned around the engagement portion 572 of the rod 570. Each prong 676 may have one or more pins 678 for engaging the flat surfaces 574 of the engagement portion 572. The pins 678 may be made of a different material than the flat surfaces 574, engagement portion 572 and/or rod 570. Specifically, the pins 678 may be made of a harder material than the flat surfaces 574, engagement portion 572 and/or rod 570 (e.g., pins 678 may be made of steel and the flat surfaces 574, engagement portion 572 and/or rod 570 may be made of titanium) for reasons which will become apparent below. The outer sleeve 674 may have a first position, where the distal end 674a of the outer sleeve 674 may be positioned away from the prongs 676, and a second position (shown in FIG. 9B), where the distal end 674a of the outer sleeve 674 may be positioned proximate (e.g., over) the prongs 676. In use, the prongs 676 may be positioned around the engagement portion 572 when the outer sleeve 652 is in the first position. In this configuration, the rod 570 may be moveable (e.g., pivotable) relative to the holding instrument 670. In order to fix the orientation of the rod 570 with respect to the holding instrument 670, the outer sleeve 674 may be moved from the first position to the second position. With the distal end 674a of the outer sleeve 674 positioned over the prongs 676, the prongs 676 and pins 678 may be compressed against the flat surfaces 574 of the engagement portion 572. In particular, when the pins 678 are made of a harder material than the flat surfaces 574, compression of the prongs 676 against the flat surfaces 574 may result in the pins 678 deforming, creating depressions/indentations in and/or digging into the flat surfaces 574, thereby fixing the position of the rod 570 relative to the holding instrument 670.

FIGS. 13A and 13B illustrate another embodiment of a rod 700 and a holding instrument 800. As shown in FIGS. 14A and 14B, the rod 700 may be a curved elongated member and may be made of a solid piece of material. Alternatively, the rod may be a straight elongated member and/or may be hollow. The rod 700 may have a proximal end 702 and a distal end 704 and may be any shape, for example, round, oval, square, rectangular or other polygon. The rod 700 may be sized and configured to be inserted through the insertion guides 200, 300, 350, guide sleeve 400 and into the channel 108 in the head portion 104 of the screw 100. The rod 700 may have an outer diameter OD7, for example, between about 3 mm and about 7 mm, more preferably, between about 5 mm and about 6.5 mm and, most preferably, between about 5.5 mm and about 6 mm. The length L7 of the rod 700 may be, for example, between about 30 mm and about 200 mm, more preferably, between about 35 mm and about 180 mm and, most preferably, between about 40 mm and about 150 mm, and the length L7 of the rod 700 may be a factor of, for example, the number of screws 100 through which the rod 700 will be inserted and/or the distance in between screws 100 (which may be dictated by patient anatomy). In an embodiment where the rod 700 is curved, the radius of the curvature R6 may be, for example, between about 50 mm and about 500 mm, more preferably, between about 80 mm and about 300 mm and, most preferably, between about 100 mm and about 200 mm.

The distal end 704 may be rounded, have a point and/or taper, which may help to move tissue around the distal end 704 as the rod 700 is inserted through the body. For example, the distal end 704 may have a radius of curvature R7 of between about 2 mm and about 15 mm, more preferably, between about 3 mm and about 12 mm and, most preferably, between about 5 mm and about 10 mm. The proximal end 702 of the rod 700 may have an engagement portion 706 which may be sized and configured so that the rod 700 may be operably attached to at least a portion (e.g., prongs 828) of the holding instrument 800. In one embodiment, the engagement portion 706 may have a circular outer shape. It should be noted, however, that other shapes may also be used. The engagement portion 706 may have one or more protrusions 708 which may engage receiving portions (e.g., recesses 830, FIG. 15B) of the holding instrument 800 such that the rod 700 may rotate about 100 degrees relative to the holding instrument 800 about an axis 710. As shown in FIGS. 14A and 14B, the protrusions 708 may have, for example, a circular shape and may engage recesses 830 which may have corresponding circular shapes.

Figure 15A:
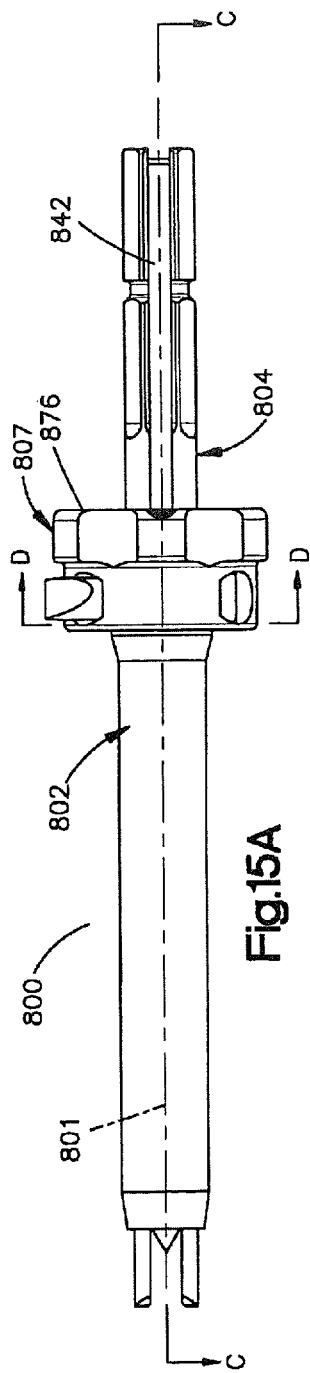
FIG. 15A is a side view of the holding instrument of FIGS. 13A and 13B.
Figure 15B:
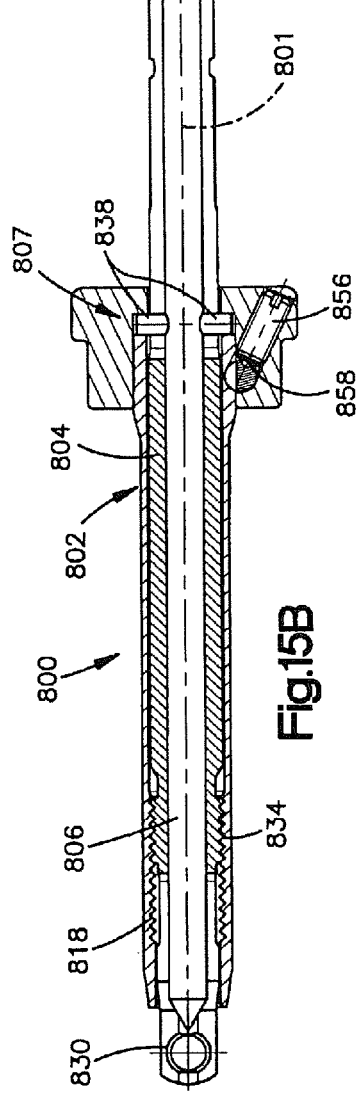
FIG. 15B is a cross-sectional view of the holding instrument of FIG. 15A along C-C.

The holding instrument 800, as depicted in FIGS. 15A and 15B, may include an outer sleeve 802, an inner sleeve 804, an elongated member 806 positioned within the inner sleeve 804 and an actuation mechanism 807 operably associated with the outer sleeve 802. The configuration of the holding instrument 800 may allow an operator to disassemble the components for a multitude of reasons including, for example, cleaning of the components.

Figure 16:
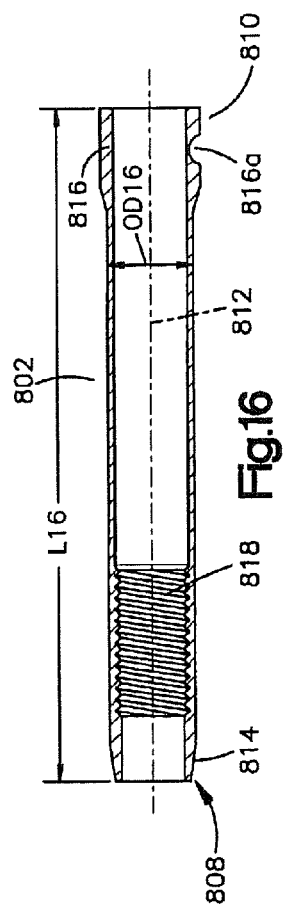
FIG. 16 is a cross-sectional view of an exemplary embodiment of an outer sleeve of the holding instrument of FIG. 15A along C-C.

As shown in FIG. 16, the outer sleeve 802 may have a distal end 808, a proximal end 810, and a channel 812 extending therethrough from the distal end 808 to the proximal end 810. In one embodiment, the outer sleeve 802 may be a cylindrical tube and may have a taper 814 at the distal end 808 which may assist in insertion of the holding instrument 800 into the body. The outer sleeve 802 may have an outer dimension OD16 of, for example, between about 3 mm and about 10 mm, more preferably, between about 4 mm and about 9 mm and, most preferably, between about 5 mm and about 8 mm and a length L16 of, for example, between about 30 mm and about 200 mm, more preferably, between about 40 mm and about 150 mm and, most preferably, between about 50 mm and about 100 mm. The proximal end 810 of the outer sleeve 802 may have an enlarged outer diameter portion 816 and may be sized and configured to fit within the actuation mechanism 806. The channel 812 may be sized and configured to receive the inner sleeve 804 such that the outer sleeve 806 may move over the inner sleeve 804. The channel 812 may have an engagement portion 818 which may engage a corresponding engagement portion 834 of the inner sleeve 804. The engagement portion 818 may have threads that would interact with corresponding threads on the engagement portion 834.

As shown in FIGS. 17A, 17B and 17C, the inner sleeve 804 may have a distal end 820, a proximal end 822 and a channel 824 extending therethrough from the distal end 820 to the proximal end 822. The inner sleeve 804 may have an outer dimension OD17 which may be sized and configured to be positioned within the channel 812 of the outer sleeve 802 so that the outer sleeve 802 and inner sleeve 804 may be moved relative to each other, rotationally and/or axially slidable. For example, the inner sleeve 804 may have an outer dimension OD17 of between about 2 mm and about 9 mm, more preferably, between about 2.5 mm and about 8 mm and, most preferably, between about 3 mm and about 7 mm. The inner sleeve 804 may have a length L17 of, for example, between about 40 mm and about 250 mm, more preferably, between about 60 mm and about 200 mm and, most preferably, between about 80 mm and about 150 mm. The proximal end 822 of the inner sleeve 804 may be sized and configured to be engaged by a tool. For example, the proximal end 822 may be hexagonal in shape and/or may have a groove 822a. The hexagonal shape and groove 822a may provide an interface for attaching various tools which an operator may use in conjunction with the holding instrument 800. In another embodiment, the proximal end 822 may be textured (e.g., knurled) to provide an enhanced grip for grasping the holding instrument 800 or may have a handle attached thereto.

Moreover, a slit 826 may pass through the distal end 820 of the inner sleeve 804 and may extend from the distal end 820 towards the proximal end 822. The slit 826 may result in the distal end 820 having at least two prongs 828 which may be flexible. The prongs 828 may have recesses 830 so that when the engagement portion 706 of the rod 700 is inserted in between the prongs 828 in the slot 826, the recesses 830 may receive the protrusions 708 of the engagement portion 706. In this way, the inner sleeve 804 and, consequently, the holding instrument 800 may be operably coupled to the rod 700. Such a construction may prevent the rod 700 and the holding instrument 800 from being separated from each other while, at the same time, may allow for rotation or pivoting of the rod 700 with respect to the holding instrument 800 about axes 710, 832. The recesses 830 may be circular in shape or any other shape (which, in some embodiments, may correspond to the shape of the protrusions 708) and may have a dimension (e.g., diameter) of, for example, between about 1 mm and about 8 mm, more preferably, between about 2 mm and about 7 mm and, most preferably, between about 3 mm and about 5 mm.

Figure 18:
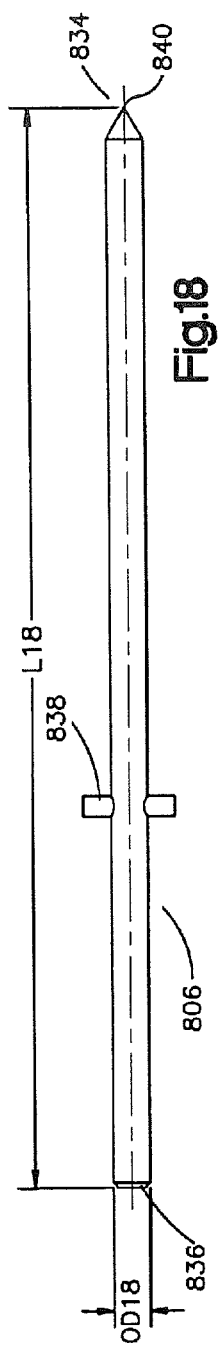
FIG. 18 is a side view of an exemplary embodiment of an elongated member of the holding instrument of FIGS. 15A and 15B.

The channel 824 of the inner sleeve 804 may be sized and configured to receive the elongated member 806 such that the elongated member 806 may be moved (rotated and/or axially slid) within the channel 824. The elongated member 806 may have a distal end 834, a proximal end 836 and at least one guide member 838 positioned between the distal end 834 and the proximal end 836. The elongated member 806 may have a cylindrical shape, however, those skilled in the art will appreciate that the member 806 may be any shape so long as it may move within the channel 824 of the inner sleeve 804. The elongated member 806 (FIG. 18) may have an outer dimension OD18 of between about 1.5 mm and about 8 mm, more preferably, between about 2 mm and about 7 mm and, most preferably, between about 2.5 mm and about 6 mm. The elongated member may have a length L18 of, for example, between about 50 mm and about 300 mm, more preferably, between about 60 mm and about 250 mm and, most preferably, between about 70 mm and about 200 mm. The distal end 834 of the elongated member 806 may be tapered so that the distal end 834 may have a point 840. Moreover, the guide member 838 may be sized and configured to move within the slots 842 of the inner sleeve 804, which may extend from the proximal end 822 towards the distal end 820 of the inner sleeve 804. The slots 842 may have a length LS of, for example, between about 5 mm and about 60 mm, more preferably, between about 10 mm and about 50 mm and, most preferably, between about 15 mm and about 40 mm. The guide member 838 may enable the elongated member 806 to translate along the axis 801 within the channel 824 of the inner sleeve 804 while preventing rotational movement of the elongated member 806 with respect to the inner sleeve 804 (i.e., about axis 801). As shown in FIG. 158, the guide member 838 may be positioned between the proximal end 810 of the outer sleeve 802 and the actuation mechanism 807.

The actuation mechanism 807 may be used to move the elongated member 806 and/or the outer sleeve 802 with respect to the inner sleeve 804. As illustrated in FIGS. 19A-19E, the actuation mechanism 806 may have a body portion 844, a first passageway 846 through the body portion 844 which may be sized and configured to receive the enlarged end 816 of the outer sleeve 802, and a second passageway 848 which may be sized and configured to receive the inner sleeve 804. Such a construction may form a shoulder 851 against which the guide member 838 and/or the proximal end 810 of the outer sleeve 802 may be placed (FIG. 15B). In this way, the outer sleeve 802 and the elongated member 806 may moved together along the axis 801 relative to the inner sleeve 804.

The body portion 844 may have a bore 850 passing therethrough, which may intersect the first passageway 846, and may be sized and configured to receive a retaining member 852 (FIGS. 19A and 19B). A further bore 854 may intersect the bore 850 and may be at an angle (e.g., about 45 degrees) with respect to the bore 850. The bore 854 may receive a holding member 856 which may engage the retaining member 852. For example, the holding member 856 may be a ball plunger which may have a spherical end 858 (FIG. 15B) which may protruded into the bore 850 and may engage the retaining member 852 and, in particular, a receiving portion 860a, 860b of the retaining member 852. In addition, the bore 854 may have threads 856 and the holding member 856 may have a threaded outer surface (not shown) for engaging the threads 856 of the bore 854. In this way, the holding member 856 may be temporarily positioned within the bore 854. Such a construction enables for disassembling/removal of the holding member 856 for cleaning of the actuation mechanism 807. In other embodiments, the holding member 856 may be permanently positioned within the bore 854 (e.g., welded, adhered) to engage the retaining member 852.

The retaining member 852 may be positioned through a recess 862 on either side of the body 844 and partially into the bore 850. The retaining member 852 may have a proximal end 864, a distal end 866 and a knob 868 on the proximal end. The knob 868, which may be tapered, may be positioned within one of the recesses 862 so that an operator may rotate the retaining member 852 relative to the body 844. The distal end 866 of the retaining member 852 may be positioned within the other recess 862 and a retaining means (e.g., ring 870) may be positioned therearound so that the retaining member 853 may be rotatably held in the bore 850. The ring 870 may engage the retaining member 852 so that ring 870 may be removable from the retaining member 852 (e.g., complementary threads on the ring 870 and the retaining member 852) to allow, for example, for cleaning of the actuation mechanism 807. In other embodiments, the ring 870 may be permanently fixed to the retaining member 852 (e.g., by laser welding). The knob 332 may have a dimension which may be larger than the dimension of the bore 850 so that the retaining member 852 may be held in the bore 850 by the knob 332 and the ring 870.

The retaining member 852 may also have a notch 872 which may be sized and configured so that the proximal end 810 of the outer sleeve 802 and, specifically, the enlarged portion 816 may be positioned therein. For example, the notch 872 may have a shape and size which may be approximately equal to the shape and radius of curvature of the enlarged portion 816 of the outer sleeve 802. The retaining member 852 may be positioned in the bore 850 such that the retaining member 852 may interact with the recess 816a of the outer sleeve 802 so that the retaining member 852 may be rotated within the bore 850 and recess 816a. When the retaining member 852 is rotated so that the notch 872 faces the recess 816a, the outer sleeve 802 and, consequently, the elongated member 806 may be freely moveable with respect to the actuation mechanism 807 (e.g., the outer sleeve 802 and/or elongated member 806 may be moveable in and out of the passageway 846 along the axis 801 and/or the outer sleeve 802 may be rotatable relative to the actuation mechanism 807). In this manner, the outer sleeve 802 and elongated member 806 may be released or disengaged from the actuation mechanism 807. The retaining member 852 may be held in this position by the holding member 856 (e.g., the spherical end 858) engaging the receiving portion 860b. When the retaining member 852 is rotated, for example, 180 degrees, so that the notch 872 faces away from the recess 816a and an outer surface 850a (e.g., a surface diametrically opposed to the notch 872) of the retaining member 852 may be positioned within the recess 816a. The retaining member 852 may prevent the outer sleeve 802 and/or elongated member 806 from moving along the axis 801 relative to the actuation mechanism 807. Moreover, the outer sleeve 802 may be prevented from rotating with respect to the actuation mechanism 807. The retaining member 852 may be held in this position by the holding member 856 (e.g., the spherical end 858) engaging the receiving portion 860a. In such a position, the actuation mechanism 807 may be used to move the outer sleeve 802 and/or the elongated member 806 relative to the inner sleeve 804 along the axis 801 and/or rotate the outer sleeve 802 about the axis 801.

In order to assist in movement of the actuation mechanism 807, the mechanism 807 may have a gripping portion 876. The gripping portion 876 may have one or more indentations 878 along the periphery of the gripping portion 876 to enhance an operator's grip on the actuation mechanism 807. In addition, the actuation mechanism 807 may have a textured surface (e.g., knurl) to enhance grip.

In order to assemble the holding instrument 800, the elongated member 806 may be inserted into the channel 824 at the proximal end 822 of the inner sleeve 804 such that the guide member 838 may be positioned within slots 842 of the inner sleeve 804. The inner sleeve 804 and elongated member 806 may be inserted as a single unit into the proximal end 810 of the outer sleeve 802. The threads 818 of the outer sleeve 802 may engage the threaded portion 834 of the inner sleeve 804 so that the outer sleeve 802 may be screwed onto the inner sleeve 804. The outer sleeve 802 may be screwed onto the inner sleeve 804 until the distal end 808 of the outer sleeve 802 may be positioned near the proximal end 828a of the prongs 828. In such a position, the prongs 828 may be flexible. The actuation mechanism 807 may then be positioned over and down the inner sleeve 804 from proximal end 822 and over the proximal end 810 (e.g., the enlarged portion 816) of the outer sleeve 802 so that the guide member 838 may be held between the shoulder 851 of the actuation mechanism 807 and the proximal end 810 of the outer sleeve 802. The proximal end 822 of the inner sleeve 804 and the proximal end 836 of the elongated member 806 may be positioned through the second passageway 848 of the actuation mechanism 807.

Figure 20A:
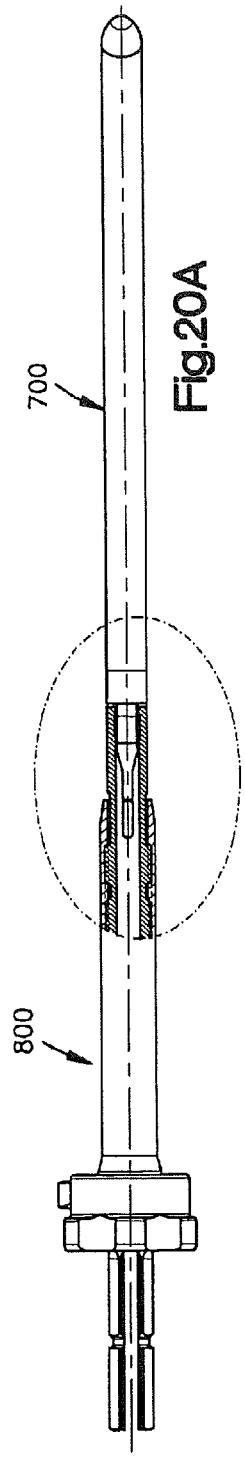
FIG. 20A is a partial cross-sectional top view of the fixation rod and holding instrument of FIG. 13A.
Figure 20B:
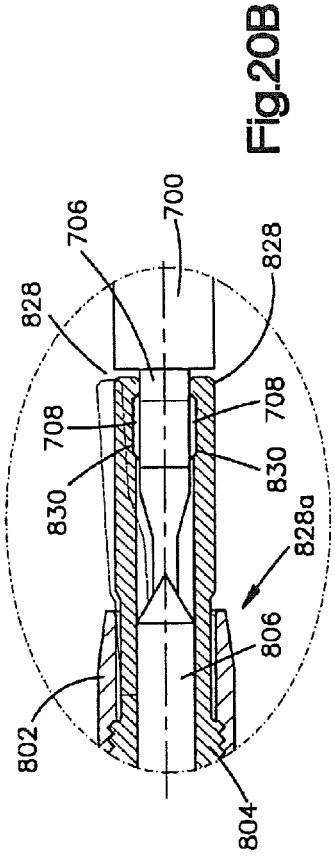
FIG. 20B is an enlarged view of a portion of FIG. 20A.

As shown in FIGS. 20A and 20B, in use, the holding mechanism 800 may engage the fixation rod 700. In particular, when the outer sleeve 802 and elongated member 806 are in a first position, the protrusions 708 of the engagement portion 706 of the rod 700 may be clipped into the recesses 830 of the prongs 828. The outer sleeve 802 and the elongated member 806 may be positioned towards the proximal ends 828a of the prongs 828. In such a position, the fixation rod 700 may be loosely held relative to the holding instrument 800. To translationally fix the orientation of the rod 700 relative to the holding instrument 800 (i.e., so that the rod 700 and holding instrument do not separate), the outer sleeve 802 may be moved (e.g., slid along, rotated about) relative to the inner sleeve 804 to a second position so that the distal end 808 of the outer sleeve 802 (FIG. 16) may be moved over the prongs 828. The actuation mechanism 807 may be used to rotate the outer sleeve 802 so that the threaded portion 818 of the outer sleeve 802 may engage threads 834 of the inner sleeve 804. Rotation of the outer sleeve 802 in a first direction (e.g., clockwise) may result in the outer sleeve 802 moving along the axis 801 towards the distal end 820 of the inner sleeve 804 and over the prongs 828. In this second position, the elongated member 806 may be positioned a distance from the rod 700, and the rod 700 may be rotatable/pivotable (e.g., about axis 832) relative to the holding instrument 800 but may not be separated from the holding instrument 800. As the distal end 808 of the outer sleeve 802 is moved farther over the prongs 828, the distal end 834 of the elongated member 806 may move axially within the inner sleeve 804 and operably engage the engagement portion 706 of the rod 700 so that the outer sleeve 802 and elongate member 806 are in a third position such as shown in FIGS. 21A and 21B.

The configuration of the elongated member 706 and rod 700 may enable an operator to fix the relationship (e.g., prevent rotation about the axis 710) of the holding instrument 800 relative to the rod 700 (e.g., the axis 801 of the holding instrument 800 may be aligned with or at an angle with respect to the axis 701 of the rod 700). In one embodiment, the rod 700 and/or engagement portion 706 of the rod 700 may be made of a soft material (e.g., titanium) and the elongated member 806 may be made of a harder material (e.g., stainless steel) such that when the elongated member 806 engages the engagement portion 706 of the rod 700, the tapered portion/tip 840 of the elongated member 806 may deform, dig-in and/or create a depression in the engagement member 706. Such a construction may create a step-less configuration (i.e., the rod 700 and the holding instrument 800 may be positioned at any angle relative to each other). In some embodiments, the engagement portion 706 of the rod 700 may have one or more receiving portions or recesses 706a positioned at predetermined intervals along the engagement portion 706 of the rod 700. Such a construction may result in a stepped configuration (i.e., the rod 700 and holding instrument 800 may be positioned at pre-set fixed angles relative to each other). In an embodiment where the engagement portion 706 of the rod 700 has only one recess 706a, the recess 706a may be positioned so that when the tapered portion/tip 840 of the elongated member 806 engages the recess 706a, the axis 701 of the rod 700 may be aligned with the axis 801 of the holding instrument 800 such as shown in FIGS. 13A and 13B. Those skilled in the art will appreciate that a combination of a step-less and stepped configuration may be used.

Figure 24:
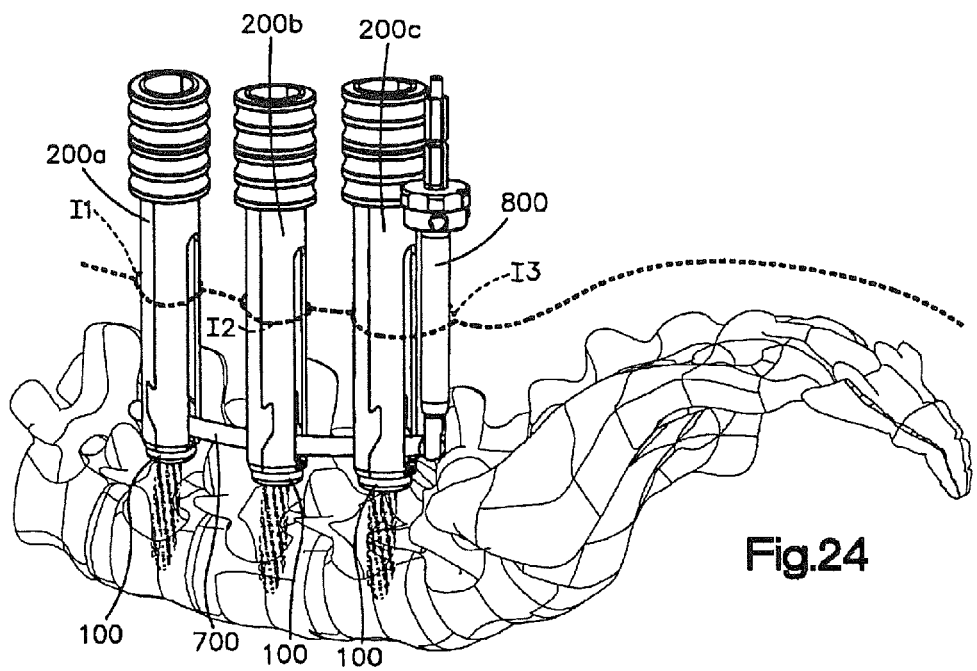
FIG. 24 is a perspective view of the fixation rod and holding instrument of FIG. 13A as the fixation rod and holding instrument are moved farther into the body.

As shown in FIGS. 22A, 23A and 24, the holding instrument 800 may be used to insert a rod 700 through insertion guides 200a, 200b and/or 200c and into the pedicle screw. It should be noted, however, that any combination of the insertion guides 200, 300, 350; rod 500, 550, 570, 700 and holding instrument 600, 650, 670, 800 may be used to perform a spinal fixation procedure. The axis 701 of rod 700 is preferably aligned with the axis 801 of the holding instrument 800. As shown in FIG. 22B, the sleeve 400 may be positioned in the bore 205 of the insertion guide 200c such that at least a portion of the first opening 408 of the sleeve 400 intersects the first longitudinal slot 212 of the insertion guide 200 to form a first window FW and the second opening 410 of the sleeve 400 intersects at least a portion of the second longitudinal slot 220 of the insertion guide 200 to form a second window SW. Preferably the first window FW is located above the skin level SL of the patient's back. As illustrate in FIG. 22C, the distal tip of the rod 700 may be passed through the first window FW, preferably above the skin level SL, into and through the bore 407 of the sleeve 400 and the bore 205 of the insertion guide 200c, and out the second window SW. If the first window FW is not located above the skin level SL, for example, due to the anatomy of a patient, a surgeon may use the rod 700 to move skin and tissue out of the way by pushing the skin down with the rod 700 so that the rod 700 may be positioned through the first window FW.

To initially move the rod 700 through the first window FW and into the body, the holding instrument 800 may be fixed with respect to the rod 800 so that the axis 701 of the rod 700 may align with the axis 801 of the holding instruments. In other embodiments, the rod 700 may be freely moveable (e.g., rotatable) with respect to the holding instrument 800. Those skilled in the art will appreciate that for some procedures, a holding instrument may be unnecessary and an operator may grasp the rod 700 with his/her fingers and move the rod 700 into the body.

When the rod 700 exits the second window SW of the first insertion guide 200c, the rod 700 is preferably below the skin level SL and/or fat layer FAL of the patient and into the tissue (i.e., muscle M) below the facia level FL (FIG. 22C). In this manner the rod 700 passes through the bore 205 of the insertion guide 200c, below the facia level FL and into the muscle M region of a patient's back. As shown in FIGS. 22A, 22B and 22C, the size and location of the windows FW, SW may enable an operator to guide the distal tip of the rod 700 out of the second window SW of the first insertion guide 200c and through tissue (at an angle) and through longitudinal slots 212, 220 in insertion guides 200a, 200b.

The different in the height H3 of the first longitudinal opening 412 and the height 114 of the second longitudinal opening 414 helps to define the angle at which the rod 700 traverses the body tissue. This angle may be chosen so that a surgeon may not insert the rod 700 too deep into the body (i.e., the angle does not allow a surgeon to insert the rod 700 too far into the vertebral bodies), thereby preventing nerve root injury. It should be noted that depth of the rod 700 in the body may also be controlled by the curvature of the rod 700 (e.g., radius of curvature R6) and/or the surgeon moving the sleeve 400 and/or the insertion guide 200c back and forth (i.e., parallel to the longitudinal axis of the spine). The configuration of the guide sleeve 400 in the insertion guide 200c may also prevent the rod 700 from being moved down the guides (e.g., guides 200b, 200c) through the first and second longitudinal slots 212, 220. A surgeon may be able to directly visualize the rod 700 being inserted through the head portions 104 of the screw 100 by looking down into the insertion guides 200a, 200b, 200c and/or sleeve 400. As the fixation rod 700 is being inserted into the body, the sleeve 400 and insertion guides 200a, 200b, 200c may be manipulated to further facilitate introduction of the rod 700 into alignment with the channel 108 of the pedicle screws 100 (e.g., to align the longitudinal slots 212, 220 of adjacent guides 200a, 200b, 200c). For example, those skilled in the art will appreciate that the insertion guide 200c, sleeve 400 and rod 700 (which has been inserted into the guide 200c and sleeve 400) may be rotated about the axis 201 (FIG. 3B) of the insertion guide 200c so that the tip of the rod 700 may be aligned with the slots 212, 220 of an adjacent insertion guide 200b. At the same time, one or more insertion guides 200a, 200b may also be rotated to assist in alignment.

As shown in FIG. 23A, once the rod 700 is positioned through all the insertion guides 200a, 200b, 200c, the rod 700 may be rotated or pivoted relative to the holding instrument 800 so that the axis 801 of the holding instrument 800 may be at an angle with respect to the axis 701 of the rod 700. In order to rotate or pivot the rod 700 relative to the holding instrument 800, the holding instrument 800 may be in the second position, described above, where the distal end 808 of the outer sleeve 802 may be moved over the prongs 828 of the inner sleeve. The holding instrument 800 may be fixed in an angular orientation with respect to the rod 700 or may be freely rotatable with respect thereto. Thereafter, as shown in FIG. 23B, the sleeve 400 may be rotated within the insertion guide 200c (e.g., about 90 degrees) so that the first longitudinal slot 212 of the guide 200c may be aligned with the first longitudinal opening 412 of the sleeve 400 and the second longitudinal slot 220 of the guide 200c may be aligned with the second longitudinal opening 414 of the sleeve 400. With the sleeve 400 in the rotated position, the rod 700 may be moved down into the body from the position shown in FIG. 23A to the position shown in FIG. 24. In particular, the rod 700 may move down the first and second longitudinal slots 212, 220 and first and second longitudinal openings 412, 414 so that the rod 700 may be positioned in the channels 108 of the head portions 104 of the screws 100. In an embodiment where separate incisions may be used, the holding instrument 800 may be inserted down the same incision 13 into which the insertion guide 200c is positioned. Such a technique for inserting a fixation rod may provide the advantage of allowing the fixation rod to be inserted into the bone screws 100 underneath the skin and muscle, without the need to make an additional incision through the skin and muscle between two or more insertion guides or between incisions.

Once the rod 700 is positioned in the channels 108 of all the screws 100, the holding instrument 800 may be detached from the rod 700 by disengaging the prongs 828 from the engagement portion 706. In order to disengage the prongs 828 of the holding instrument 800 from the engagement portion 706 of the rod 700, the outer sleeve 802 may be rotated in a second direction (e.g., counterclockwise) so that the outer sleeve 802 may be moved along the axis 801 towards the proximal end 822 of the inner sleeve 804. The holding instrument 800 may then be removed from the rod 700. The sleeve 400 may be removed from the insertion guide 200c before or after the holding instrument 800 is removed from the body or at any time after the rod 700 is positioned within the channels 108 of the screws 100.

Figure 25:
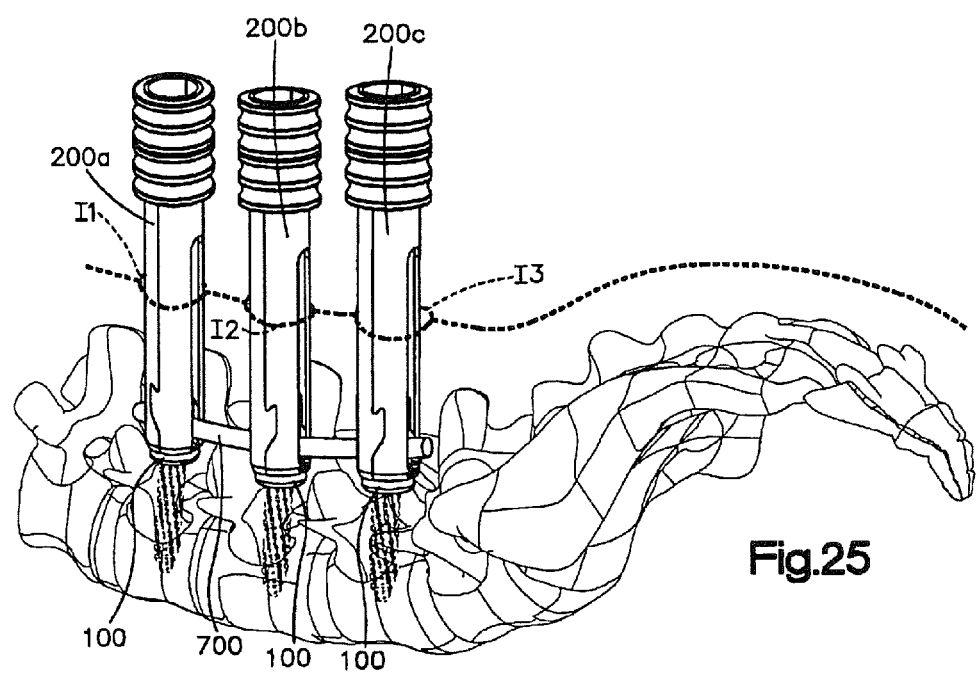
FIG. 25 is a perspective view of the spine and assemblies of FIG. 3A after a fixation rod has been positioned in the implants of FIG. 1.

As shown in FIG. 25, with the rod 700 positioned in the channels 108 of the screws 100, an end cap 150 (FIG. 26) may be inserted down the insertion guides 200a, 200b, 200c and into the head portion 104 of the screw 100. The end cap 150, for example, may be threaded and may engage the threaded portion 110 of the head portion 104. Other types of caps and engagement mechanisms between the cap and the head portion 104 of the screw 100 may be used. Thereafter, the insertion guides 200a, 200b, 200c may be detached from the screw 100 and removed from the body. In order to detach the guides 200a, 200b, 200c from head portion 104, an operator may move the ring portions 210, 218 apart so that the protrusions 222 disengage from the receiving portion 224. The guides 200a, 200b, 200c may then be removed from the body. In some embodiments, the end cap 150 may be inserted into the head portion 104 after the insertion guides have been removed from the body. With the end caps 150 in the head portion 104, the rod 700 may be held firmly in place between the end caps 150 and the surface 112a, 112b and may form a fixation system. It will be appreciated by those skilled in the art that any end cap (e.g., nut, clip, etc.) may be used so long as it may hold a fixation rod to a screw 100.

Those skilled in the art will also appreciate that a rod 500, 550, 570 and holding instrument 600, 650, 670 may be used to perform the procedure described above. Additionally, insertion guides 300, 350 may be used in place of or in combination with insertion guides 200. Also, sleeve 416 may be used in place of sleeve 400. Moreover, the present invention contemplate the use of any insertion guide, sleeve, fixation rod and/or holding instrument to perform the procedure described above.

As will be appreciated by those skilled in the art, any or all of the instrumentation describe herein such as, for example, implants (e.g., screws 100), insertion guides 200, 300, 350, sleeve 400, 416, rod (e.g., a fixation rod 500, 550, 570, 700), holding instrument 600, 650, 670, 800 and/or components of any of the instrumentation may be provided in sets or kits so that the a surgeon may select various combinations of components to perform a fixation procedure and create a fixation system which is configured specifically for the particular needs/anatomy of a patient. It should be noted that one or more of each instrument and/or their components may be provide in a kit or system. In some kits or sets, the same device may be provided in different shapes and/or sizes (e.g., multiple screws 100, insertion guides 200, 300, 350 and/or rods 500, 550, 570, 700 of different sizes).

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A system for performing spinal fixation comprising:
at least one elongated fixation member;
at least one screw including a threaded shaft portion and a head portion having two arms forming a U-shaped channel capable of receiving the elongated fixation member;
a plurality of attachment members, each having at least an elongated body, an outer wall, an inner wall, a proximal end, and a distal end, wherein each distal end is selectively attachable to the head portion of the screw,
wherein at least two attachment members are each attachable to each one of the two arms of the head portion of one of said screws to form a first longitudinal slot diametrically opposed from a second longitudinal slot, and a longitudinal space between the inner walls of the at least two attachment members, the longitudinal space extending from the distal ends towards the proximal ends of the at least two attachment members;
and,
a sleeve comprising
an elongated body,
a proximal end,
a distal end,
a bore extending from the proximal end to the distal end,
first and second openings in said elongated body,
a first longitudinal slot extending from the first opening to the distal end of the sleeve and a second longitudinal slot extending from the second opening to the distal end of the sleeve,
wherein the sleeve is sized to be received within the longitudinal space formed by the at least two attachment members, wherein the sleeve is configured such that when the sleeve is received within the longitudinal space formed by the at least two attachment members, the first opening of said sleeve may be aligned with the first longitudinal slot of said attachment members to form a first window, and the second opening of said sleeve may be aligned with the second longitudinal slot of said attachment members to form a second window, the first and second windows being sized and configured to receive a fixation member therethrough, and, wherein the first longitudinal slot of the sleeve is angled with respect to the first opening of the sleeve, and the second longitudinal slot of the sleeve is angled with respect to the second opening of the sleeve.

2. The system of claim 1, wherein the longitudinal slots formed by the attachment members are aligned with the U-shaped channel.

3. The system of claim 1, wherein the longitudinal slots formed by the attachment members extend longitudinally from the distal end of the attachment members toward the proximal end.

4. The system of claim 1, wherein the longitudinal slots formed by the attachment members communicate with the longitudinal space.

5. The system of claim 1, wherein the longitudinal slots formed by the attachment members extend from the outer wall through the inner wall of the attachment members.

6. The system of claim 1, wherein the longitudinal slots formed by the attachment members are sized to receive the elongated fixation member therethrough.

7. The system of claim 1, wherein the head portion of the screw is polyaxially coupled to the shaft portion.

8. The system of claim 1, further comprising a holding instrument for engaging the elongated fixation member.

9. The system of claim 8, wherein the holding instrument further comprises an end portion with a plurality of recessed edges for improving hand grip.

10. The system of claim 8, wherein the holding instrument is pivotally engageable with the elongated fixation member.

11. The system of claim 1, further comprising a substantially circular member in slidable contact with the outer wall of at least one of the attachment members.

12. The system of claim 1, further comprising a threaded end cap capable of selectively engaging the screw head portion for securing the elongated fixation member.

13. The system of claim 1, wherein the attachment members have relatively thin side walls between the outer wall and the inner wall.

14. The system of claim 13, wherein the longitudinal slots formed by the attachment members are formed between the side walls of the attachment members when each of the first and second members are selectively engaged with at least one of the arms of the head portion of the screw.

15. A system for performing spinal fixation comprising:
at least one elongated fixation member;
a plurality of screws including a threaded shaft portion and a head portion having two arms forming a U-shaped channel capable of receiving the elongated fixation member, the arms having an interior and exterior surface, wherein each arm of the head portion has a recessed area and the interior surface is at least partially threaded;
a plurality of attachment members, each having at least an elongated body, an outer wall, an inner wall, a proximal end, and a distal end, wherein each distal end is selectively engageable with at least one arm of the head portion of the screw,
wherein each attachment member is configured with flanges at its distal end for selective snap-fit attachment with one of the arms of the head portion of the screw, and,
wherein at least two attachment members are each attachable to each one of the two arms of the head portion to form a first longitudinal slot diametrically opposed from a second longitudinal slot, and a longitudinal space between the inner walls of the two attachment members, the longitudinal space extending from the distal ends towards the proximal ends of the two attachment members;
and,
a sleeve comprising
an elongated body,
a proximal end,
a distal end,
a bore extending from the proximal end to the distal end,
first and second openings in said elongated body,
a first longitudinal slot extending from the first opening to the distal end of the sleeve and a second longitudinal slot extending from the second opening to the distal end of the sleeve,
wherein the sleeve is sized to be received within the longitudinal space formed by the at least two attachment members,
wherein the sleeve is configured such that when the sleeve is received within the longitudinal space formed by the at least two attachment members, the first opening of said sleeve may be aligned with the first longitudinal slot of said attachment members to form a first window, and the second opening of said sleeve may be aligned with the second longitudinal slot of said attachment members to form a second window, the first and second windows being sized and configured to receive a fixation member therethrough,
and,
wherein the first longitudinal slot of the sleeve is angled with respect to the first opening of the sleeve, and the second longitudinal slot of the sleeve is angled with respect to the second opening of the sleeve.

16. A system for performing spinal fixation comprising:
at least one elongated fixation member;
a plurality of screws including a threaded shaft portion and a head portion, polyaxially coupled to the shaft portion, having two arms forming a U-shaped channel capable of receiving the elongated fixation member, the arms having an interior and exterior surface, wherein each arm of the head portion has a recessed area and the interior surface is at least partially threaded;
a plurality of attachment members, each having at least an elongated body, an outer wall, an inner wall, a plurality of relatively thin side walls between the outer wall and inner wall, a proximal end, and a distal end, wherein each distal end is selectively engageable with at least one arm of the head portion of the screw,
wherein each attachment member is configured with flanges at its distal end for selective snap-fit attachment with one of the arms of the head portion of the screw,
wherein at least two attachment members are each attachable to each one of the two arms of the head portion to form a first longitudinal slot diametrically opposed from a second longitudinal slot, wherein the longitudinal slots are aligned with the U-shaped channel, and extend longitudinally from the distal end of the attachment members toward the proximal end, and extend from the outer wall through the inner wall of the attachment members, and are sized to receive the elongated fixation element therethrough;

a longitudinal space between the inner walls of the two attachment members, the longitudinal space extending from the distal ends towards the proximal ends of the two attachment members, wherein the longitudinal slots communicate with the longitudinal space;

a circular member in slidable contact with the outer wall of at least one of the attachment members;

a threaded end cap capable of selectively engaging the screw head portion for securing the elongated fixation member;

and, a sleeve comprising
- an elongated body,
- a proximal end,
- a distal end,
- a bore extending from the proximal end to the distal end,
- first and second openings in said elongated body,
- a first longitudinal slot extending from the first opening to the distal end of the sleeve and a second longitudinal slot extending from the second opening to the distal end of the sleeve, wherein the sleeve is sized to be received within the longitudinal space formed by the at least two attachment members, wherein the sleeve is configured such that when the sleeve is received within the longitudinal space formed by the at least two attachment members, the first opening of said sleeve may be aligned with the first longitudinal slot of said attachment members to form a first window, and the second opening of said sleeve may be aligned with the second longitudinal slot of said attachment members to form a second window, the first and second windows being sized and configured to receive a fixation member therethrough, and, wherein the first longitudinal slot of the sleeve is angled with respect to the first opening of the sleeve, and the second longitudinal slot of the sleeve is angled with respect to the second opening of the sleeve.

* * * * *